United States Patent
Sato

(10) Patent No.: US 9,119,584 B2
(45) Date of Patent: Sep. 1, 2015

(54) RADIATION IMAGE CAPTURE DEVICE

(71) Applicant: FUJIFILM Corporation, Tokyo (JP)

(72) Inventor: Keiichiro Sato, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 262 days.

(21) Appl. No.: 13/653,281

(22) Filed: Oct. 16, 2012

(65) Prior Publication Data

US 2013/0099129 A1 Apr. 25, 2013

(30) Foreign Application Priority Data

Oct. 19, 2011 (JP) .................................. 2011-230044

(51) Int. Cl.
- *A61B 6/00* (2006.01)
- *G01T 1/24* (2006.01)
- *H04N 5/32* (2006.01)
- *H01L 27/146* (2006.01)

(52) U.S. Cl.
CPC ............. *A61B 6/4225* (2013.01); *A61B 6/4233* (2013.01); *A61B 6/4283* (2013.01); *G01T 1/24* (2013.01); *G01T 1/247* (2013.01); *H01L 27/14609* (2013.01); *H01L 27/14618* (2013.01); *H04N 5/32* (2013.01); *A61B 6/4208* (2013.01)

(58) Field of Classification Search
USPC ..................................................... 250/370.09
See application file for complete search history.

(56) References Cited

FOREIGN PATENT DOCUMENTS

| | | | |
|---|---|---|---|
| JP | 05-259591 A | 10/1993 | |
| JP | 2002-158341 A | 5/2002 | |
| JP | 2006-112803 A | 4/2006 | |
| JP | 2006-148005 A | 6/2006 | |
| JP | 2006-250899 A | 9/2006 | |
| JP | 2010-197404 A | 9/2010 | |
| JP | 2010-264250 A | 11/2010 | |
| JP | 2011-95166 A | 5/2011 | |
| JP | 2011095166 A | * 5/2011 | |

OTHER PUBLICATIONS

Notification of Reason(s) for Rejection dated Oct. 8, 2013, with English translation.
Japanese Office Action dated Jul. 1, 2014 with partial English Translation.

* cited by examiner

*Primary Examiner* — Christine Sung
(74) *Attorney, Agent, or Firm* — McGinn IP Law Group, PLLC

(57) ABSTRACT

A radiation image capture device is provided with a radiation detection panel including optoelectronic conversion elements, a signal processing board that performs signal processing of the signals provided by the radiation detection panel, a flexible printed circuit, and a casing. One end of the flexible printed circuit is connected to the radiation detection panel and the other end is connected to the signal processing board. The flexible printed circuit includes a base film fowled of an insulating resin film, wiring disposed over the base film, a coating layer formed of an insulating resin disposed over the wiring, and a shield layer provided between the base film and the wiring and/or between the wiring and the coating layer. An insulator is interposed between the shield layer and the wiring, and the shield layer is connected to a fixed potential.

20 Claims, 13 Drawing Sheets

RADIATION IMAGE CAPTURE DEVICE

CROSS-REFERENCE TO RELATED APPLICATION

This application is based on and claims priority under 35 USC 119 from Japanese Patent Application No. 2011-230044 filed on Oct. 19, 2011, which is incorporated by reference herein.

BACKGROUND

1. Technical Field

The present invention relates to a radiation image capture device, and particularly relates to a radiation image capture device in which a radiation detection panel and a signal processing board are connected by a flexible printed circuit (FPC).

2. Related Art

In recent years, radiation image detectors such as flat panel detectors (FPD) and the like have been realized. In an FPD, a radiation-sensitive layer is disposed on a thin film transistor (TFT) active matrix substrate, and the FPD is capable of converting radiation directly to digital data. A radiation image capture device that uses this radiation detector has the advantage, over prior art radiation image capture devices that use X-ray films, imaging plates and the like, that images may be continuously checked. This device also has the advantage of being able to perform radioscopic imaging (video imaging) in which radiation images are successively imaged.

Diverse types of this kind of radiation detector have been proposed. For example, a radiation detector that employs an indirect conversion system converts the radiation to light using a scintillator, converts the converted light to electronic charges with sensor portions such as photodiodes or the like, and accumulates these charges. The accumulated charges are data about an image captured by X-ray imaging. CsI:Tl, GOS ($Gd_2O_2S$:Tb) or the like is used for the scintillator. A radiation image capture device reads out the charges accumulated in the radiation detector in the form of analog signals, amplifies the analog signals with amplifiers, and then converts the analog signals to digital data with an analog-digital (A/D) converter.

The radiation detector is provided with a sensor portion and a signal processing board. The signal processing board performs driving control of the sensor portion and performs signal processing of captured image data provided from the sensor portion. The signal processing board is disposed to oppose the sensor portion, and the sensor portion and signal processing board are connected using a flexible printed circuit.

Portable radiation image detectors (electronic cassettes) are in high demand because of their ease of handling. Japanese Patent Application Laid-Open (JP-A) No. 2010-264250 discloses an X-ray imaging device that detects when irradiations of radiation start and stop and the like, and that does not require control for synchronization with radiation generation timings. In association with adjustments of position and posture of an imaging subject (a patient) during and before X-ray imaging, this kind of X-ray imaging device is subjected to contact with the imaging subject and impacts and the like. At such times, the flexible printed circuit touches or rubs against an interior wall of a casing that accommodates the sensor portion and the signal processing board, electrostatic charging occurs at wiring of the flexible printed circuit, and counter (compensation) charges are produced. These counter charges cause changes in the analog signals being propagated in the wiring of the flexible printed circuit, leading to misdetections of the captured X-ray image data. In a flexible printed circuit at which amplifiers are mounted, analog signal charges that have not yet been converted to analog signal voltages by the amplifiers are vulnerable to the effects of electrostatic charging.

Similarly, in an X-ray imaging device that requires control for synchronization with radiation generation timings, if electrostatic charging occurs at wiring in a flexible cable, there are changes in the analog signals during a readout of captured X-ray image data. These changes in the analog signal appear as noise in captured X-ray images.

JP-A No. 5-259591 discloses a flexible printed circuit in which a copper layer is applied to a plastic film, and a flexible printed circuit in which an antistatic layer is formed on a plastic film and the antistatic layer is covered with a protective layer. These flexible printed circuits are useful in regard to suppressing electrostatic charging.

However, in the above-mentioned flexible printed circuit in which a copper layer is applied, the copper layer detaches if it touches the casing, and it is hard to maintain the electrostatic charging suppression effect. This detachment is less likely if the thickness of the copper layer is increased, but an increase in thickness of the copper layer increases stiffness and impairs the flexibility of the flexible printed circuit.

Further, in the above-mentioned flexible printed circuit in which an antistatic layer is formed, the decay time of electrostatic charges is long, and the charges act as stray capacitances on the wiring. The stray capacitances cause changes in the analog signals being propagated in the wiring of the flexible printed circuit, leading to misdetections of captured X-ray image data. The stray capacitances also cause changes in time constants, leading to delays of the analog signals being propagated in the wiring.

SUMMARY

In consideration of the situation described above, the present invention solves the above problem and provides a radiation image capture device that may suppress electrostatic charging associated with touching and rubbing caused by movements of a flexible printed circuit.

A radiation image capture device according to a first aspect of the present invention includes: a radiation detection panel including optoelectronic conversion elements that convert radiation to electronic signals; a signal processing board disposed to oppose the radiation detection panel, the signal processing board performing signal processing of the electronic signals provided by the radiation detection panel; a flexible printed circuit of which one end is electrically connected to the radiation detection panel and another end is electrically connected to the signal processing board, the flexible printed circuit including a base film formed of an insulating resin film, wiring disposed over the base film, a coating layer formed of an insulating resin disposed over the wiring, and a shield layer provided at least one of between the base film and the wiring or between the wiring and the coating layer, an insulator being interposed between the shield layer and the wiring, and the shield layer being connected to a fixed potential; and a casing that accommodates the radiation detection panel, the signal processing board and the flexible printed circuit.

BRIEF DESCRIPTION OF THE DRAWINGS

Exemplary embodiments of the present invention will be described in detail based on the following figures, wherein.

DETAILED DESCRIPTION

Figure 1:
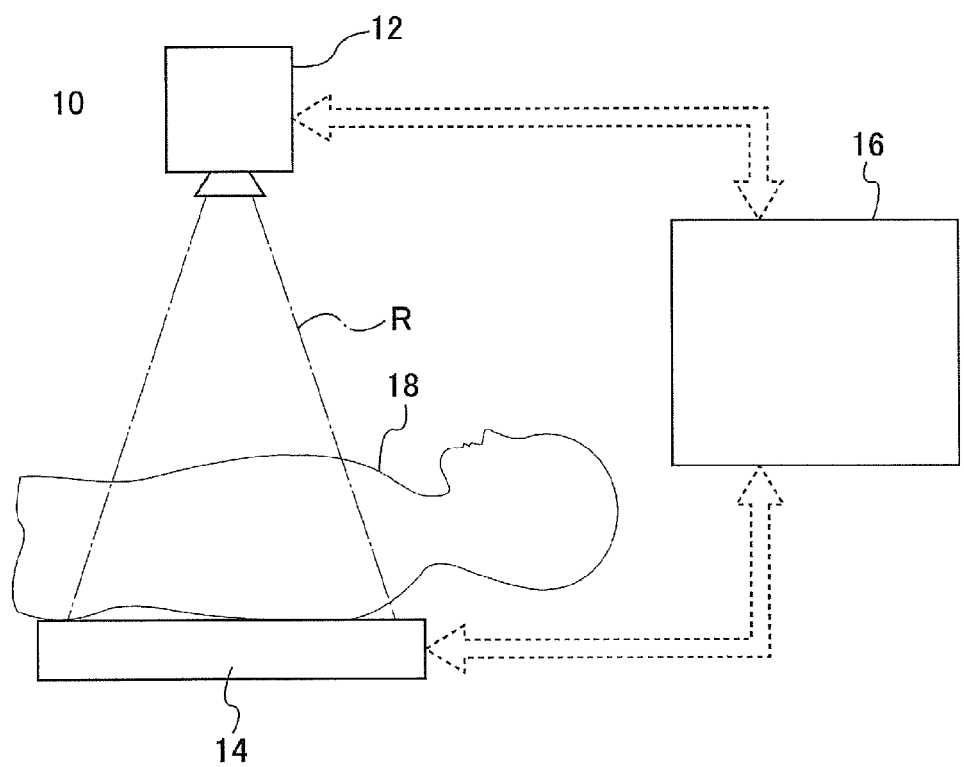
FIG. 1 is a conceptual diagram describing overall structure of a radiation image capture device in accordance with a first exemplary embodiment of the present invention.

Herebelow, exemplary embodiments in accordance with the present invention are described with reference to the attached drawings. Herein, structural elements that have the same functions are assigned the same reference numerals in the drawings, and duplicative descriptions are omitted as appropriate.

—First Exemplary Embodiment—

A first exemplary embodiment of the present invention illustrates an example of application of the invention to a portable radiation image detector (electronic cassette) that constitutes the radiation image capture device.

—Overall Structure of the Radiation Image Capture Device—

As illustrated in FIG. 1, a radiation image capture device 10 according to the first exemplary embodiment is equipped with a radiation generation device 12, a radiation image detector (electronic cassette) 14 and a console 16. The radiation generation device 12 generates radiation R and irradiates the radiation R at an imaging subject (a patient of whom a radiation image is to be captured) 18. The radiation image detector 14 generates radiation image data obtained from the radiation R transmitted through the imaging subject 18. The radiation image detector 14 is of a portable type that may be carried freely. The console 16 functions to control driving of the radiation generation device 12 and the radiation image detector 14, memorize the radiation image data generated by the radiation image detector 14, display the radiation image data, and suchlike.

In this first exemplary embodiment, the radiation image detector 14 may or may not be equipped with a function for memorizing radiation image data.

—External Structure of the Radiation Image Detector—

Figure 2:
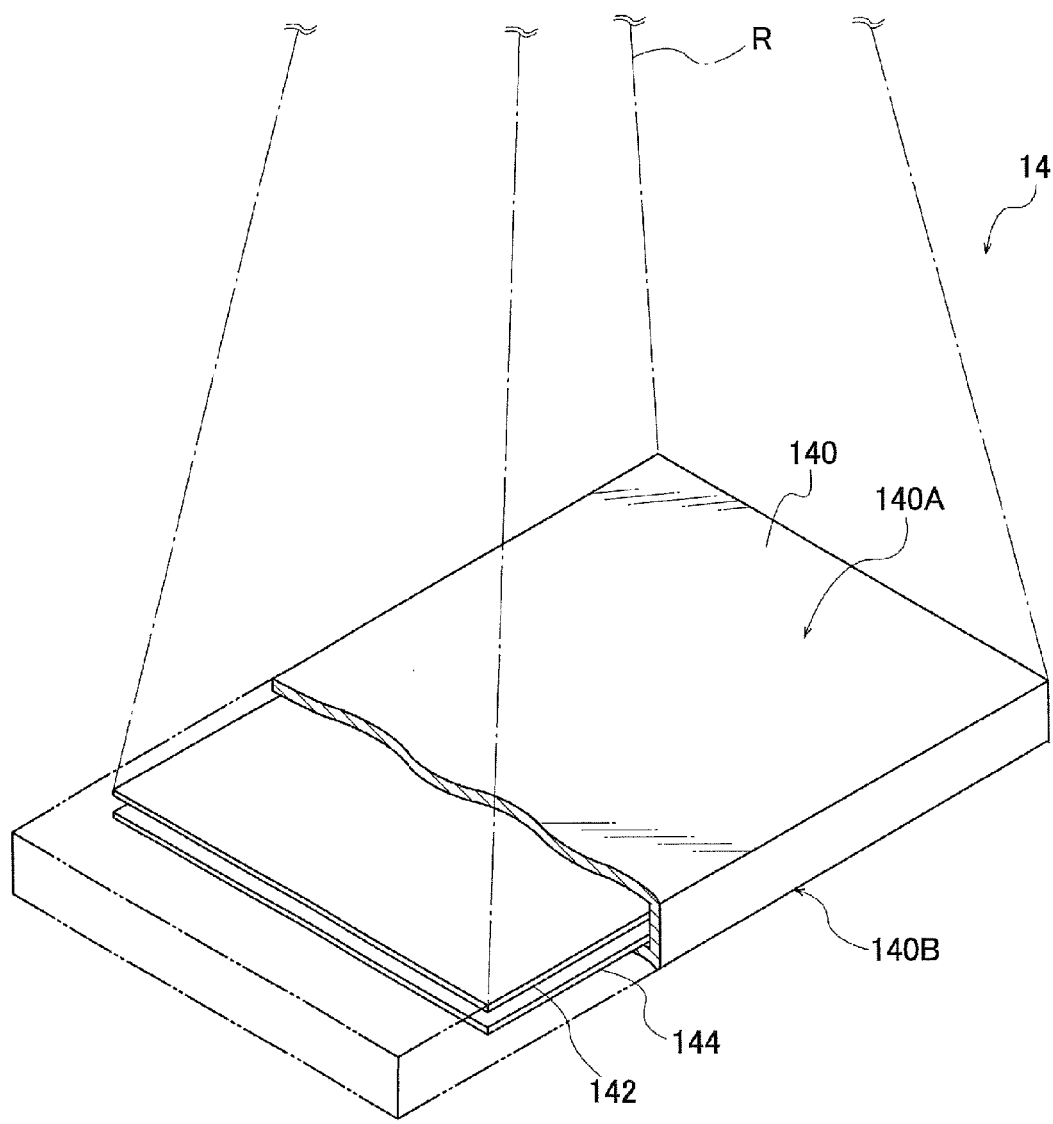
FIG. 2 is a perspective diagram of a radiation image detector (electronic cassette) of the radiation image capture device in accordance with the first exemplary embodiment, in which an appropriate portion of a casing of the radiation image detector is cut away.

As illustrated in FIG. 2, the radiation image detector 14 is provided with a casing 140 in a flat board shape with a predetermined thickness in a direction of irradiation of the radiation R. The casing 140 includes an irradiated surface 140A at the face of a side of the casing 140 that opposes the radiation generation device 12. The irradiated surface 140A is fabricated of a material that transmits at least the radiation R.

A radiation detection panel 142 and a signal processing board 144 are accommodated inside the casing 140. The radiation detection panel 142 is disposed at the irradiated surface 140A side of the casing 140, that is, the side opposing the radiation generation device 12, and the signal processing board 144 is disposed at the side of a non-irradiated surface 140B that is opposite from the irradiated surface 140A. The radiation detection panel 142 functions to generate radiation image data from the radiation R irradiated from the radiation generation device 12 and transmitted through the imaging subject 18. The signal processing board 144 functions to control driving of the radiation detection panel 142, and transmit the radiation image data generated by the radiation detection panel 142 to the console 16.

—System Structure of the Radiation Image Detector—

Figure 3:
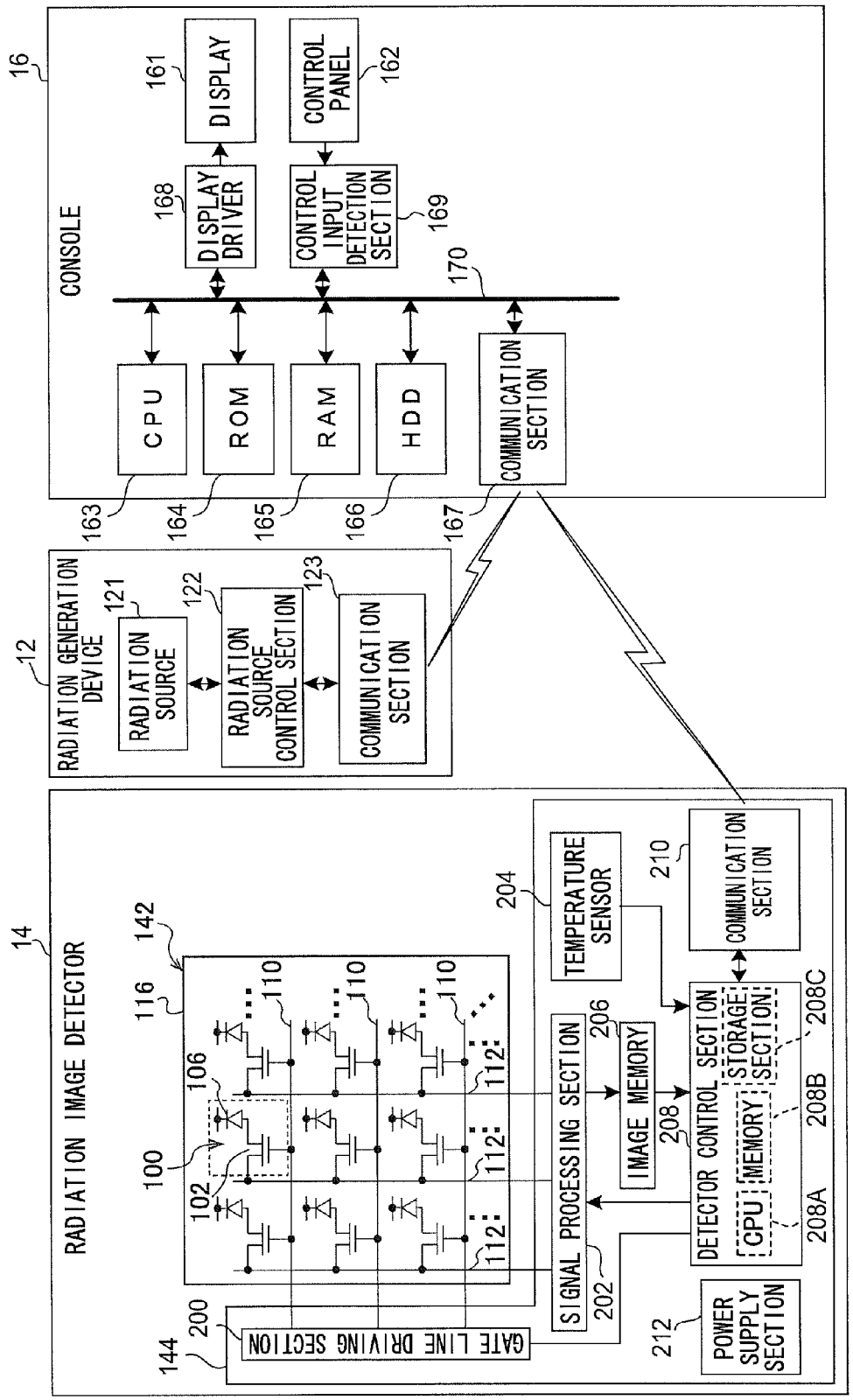
FIG. 3 is an overall block circuit diagram of the radiation image capture device in accordance with the first exemplary embodiment.

1. System Structure of the Radiation Detection Panel As illustrated in FIG. 3, the radiation detection panel 142 of the radiation image detector 14 is equipped with a TFT matrix board 116. The TFT matrix board 116 is provided with plural gate lines 110 and plural data lines 112. The gate lines 110 extend in a scanning line direction and are arrayed with a constant spacing in a signal line direction. The data lines 112 extend in the signal line direction and are arrayed with a constant spacing in the scanning line direction. Detection elements 100 are disposed at intersection portions of the gate lines 110 and data lines 112. Each detection element 100 detects light converted from the radiation R (radiation image data), converts the light to electronic signals, and then temporarily accumulates (stores) the electronic signals.

The detection element 100 is provided with a thin film transistor (TFT) 102 and an optoelectronic conversion element 106, and is constituted as a circuit with the TFT 102 and the optoelectronic conversion element 106 in parallel. One main electrode of the TFT 102 (the drain electrode, with reference numeral 102E in FIG. 6) is connected to the data line 112, and the other (the source electrode, with reference numeral 102D in FIG. 6) is connected with one electrode of the optoelectronic conversion element 106 (reference numeral electrode 106A in FIG. 5). The gate electrode of the TFT 102 (reference numeral 102A in FIG. 6) is connected to the data line 112. The TFT 102 is a switching element that switches between a conducting state (On) and a non-conducting state (Off) in accordance with driving signals supplied to the gate electrode. Another electrode of the optoelectronic conversion element 106 (reference numeral 106E in FIG. 5) is connected to a fixed potential. The optoelectronic conversion element 106 converts light signals, which are the radiation image data converted from the radiation R, to electronic signals and temporarily accumulates the converted radiation image data in the form of electrical charges.

2. System Structure of the Signal Processing Board

The signal processing board 144 of the radiation image detector 14 is provided with a gate line driving section 200, a signal processing section 202, a temperature sensor 204, an image memory 206, a detector control section 208, a communication section 210 and a power supply section 212.

The gate line driving section 200 is connected to the gate lines 110 extending across the TFT matrix board 116, and supplies driving signals for the TFTs 102 to the gate lines 110. According to the drawing in FIG. 3, the gate line driving section 200 is disposed along one edge of the TFT matrix board 116 (the left edge in this drawing) at the outer side of the edge. In practice, because the signal processing board 144 is disposed to oppose the radiation detection panel 142, the gate line driving section 200 is disposed along the one edge of the TFT matrix board 116 at the non-irradiated surface 140B side of the TFT matrix board 116 and is superposed with the edge.

The signal processing section 202 is connected to the data lines 112 that extend across the TFT matrix board 116, and acquires radiation image data read from the detection elements 100 via the data lines 112. Similarly to the gate line driving section 200, according to the drawing in FIG. 3, the signal processing section 202 is disposed along another edge (the lower edge in this drawing) adjoining the one edge of the TFT matrix board 116, at the outer side of the other edge. In practice, because the signal processing board 144 is disposed to oppose the radiation detection panel 142, the signal processing section 202 is disposed along the other edge of the TFT matrix board 116 at the non-irradiated surface 140B side of the TFT matrix board 116 and is superposed with the other edge. As well as the gate line driving section 200 and the signal processing section 202, components, circuits and systems mounted at the signal processing board 144 are disposed to be superposed with the TFT matrix board 116.

When a radiation image is captured and radiation image data is accumulated at the radiation detection panel 142, firstly, one of the gate lines 110 is selected using the gate line driving section 200, and a driving signal is supplied to this gate line 110. The TFTs 102 of all the detection elements 100 connected to this gate line 110 are put into the conducting state by the supply of the driving signal, and the radiation image data that has been temporarily accumulated in the optoelectronic conversion elements 106 is read out to the signal processing section 202 via the data lines 112. In the signal processing section 202, the charges are accumulated at sample-hold circuits (charge amplifiers, with reference numeral 220 in FIG. 4) that are provided in respective correspondence with the individual data lines 112.

The signal processing section 202 selects the sample-hold circuits 220 successively in the scanning line direction, and successively reads out the radiation image data accumulated in the sample-hold circuits 220. When the radiation image data accumulated at all of the detection elements 100 connected to the one selected gate line 110 has been read out, the gate line driving section 200 selects the succeeding gate line 110 in the signal line direction. By the same processing sequence, the signal processing section 202 successively selects the sample-hold circuits 220, and reads out the radiation image data accumulated at the detection elements 100 connected to this selected gate line 110. When all the radiation image data accumulated at the radiation detection panel 142 is read out, the radiation image data may be acquired as electronic signals (electronic data) captured in two dimensions.

Figure 4:
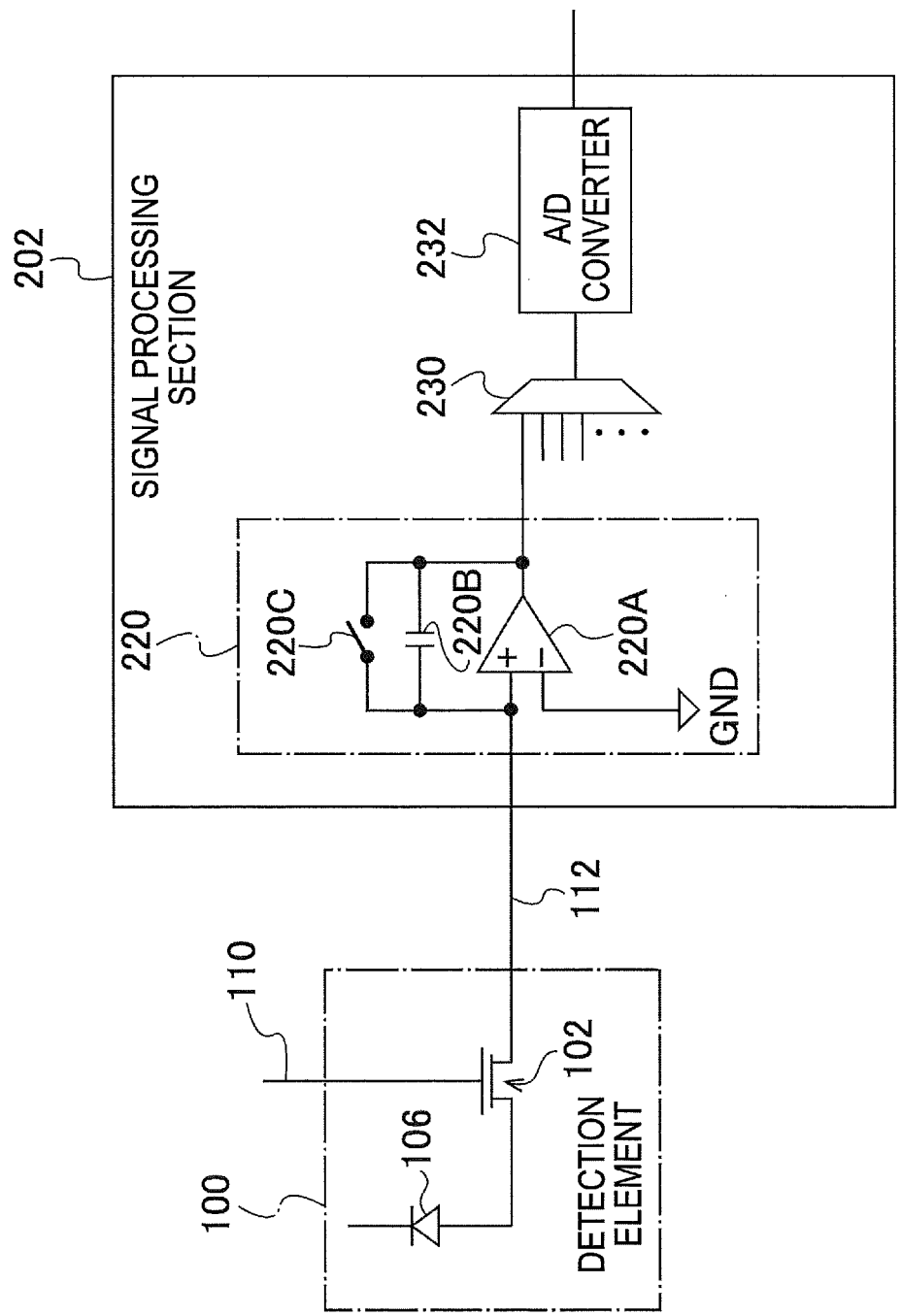
FIG. 4 is a circuit diagram of principal portions of a detection unit and a signal processing section of a radiation detection panel illustrated in FIG. 3.

As illustrated in FIG. 4, the signal processing section 202 is equipped with the sample-hold circuits 220, a multiplexer 230 and an analog-digital (A/D) converter 232. Each sample-hold circuit 220 is connected to the respective data line 112, and is provided with an operational amplifier 220A, a capacitor 220B and a switch 220C. The radiation image data (charge signals) propagated through the data lines 112 from the detection element 100 is retained at the sample-hold circuit 220. The sample-hold circuit 220 converts the charge signals to analog signals (voltage signals, which are the radiation image data) with the operational amplifier 220A and the capacitor 220B. That is, the sample-hold circuit 220 functions as a charge amplifier that converts the charges accumulated at the detection elements 100 to voltages. The switch 220C of the sample-hold circuit 220 is electrically connected between the electrodes of the capacitor 220B, in parallel with the capacitor 220B, and is used as a reset circuit that discharges charge signals accumulated at the capacitor 220B.

The analog signals converted at the sample-hold circuits 220 (output signals) are serially inputted to the multiplexer 230. The multiplexer 230 serially outputs analog signals to the A/D converter 232. The A/D converter 232 successively converts the serially inputted analog signals to digital signals (which are the radiation image data).

As illustrated in FIG. 3, the signal processing section 202 is connected to the image memory 206. The radiation image data converted to digital signals by the A/D converter 232 of the signal processing section 202 is serially memorized in the image memory 206. The image memory 206 is provided with a storage capacity capable of memorizing a predetermined number of frames of image data. Each time a radiation image is captured, the radiation image data obtained by the radiation image capture is sequentially stored in the image memory 206.

The detector control section 208 is connected to the gate line driving section 200, the signal processing section 202, the temperature sensor 204, the image memory 206, the communication section 210 and the power supply section 212, and administers control of the same. The detector control section 208 is equipped with a microcomputer, which is constituted with a central processing unit (CPU) 208A, memory 208B and a storage section 208C. The memory 208B is equipped with read-only memory (ROM) that stores a processing program that implements control of the radiation image detector 14, and the like, and random access memory (RAM) that temporarily stores various processing programs, data during processing and the like. The storage section 208C is constituted with non-volatile flash memory or the like that stores data such as the radiation image data stored in the image memory 206 and the like.

The temperature sensor 204 measures the temperature of the radiation image detector 14 and, in the first exemplary embodiment, the temperature of a central region of a lower face of the luminescent body 148 (the face at the non-irradiated surface 140B side thereof). Data on temperatures measured by the temperature sensor 204 is sent to the detector control section 208.

The communication section 210 exchanges various kinds of data with external equipment in accordance with control from the detector control section 208. The communication section 210 according to the first exemplary embodiment is a wireless communications unit complying with wireless LAN (local area network) standards, as typified by IEEE (Institute of Electrical and Electronics Engineers) 802.11a/b/g and the like. The communication section 210 transfers various kinds of data by wireless communications. Specifically, the communication section 210 exchanges various kinds of data for control relating to the capture of radiation images between the detector control section 208 and the console 16, transmits radiation image data from the detector control section 208 to the console 16, and the like.

The power supply section 212 supplies electrical power to the various circuits of the gate line driving section 200, the signal processing section 202, the image memory 206, the detector control section 208 and the communication section 210. In the first exemplary embodiment, the power supply section 212 incorporates a battery (a rechargeable battery), in order to enhance portability of the radiation image detector 14. Power is supplied from this battery to the various circuits. When the radiation image detector 14 is not in use, the battery is connected to a power supply via an unillustrated charger and is charged up.

The radiation image detector 14 according to the first exemplary embodiment employs a non-synchronous system (a synchrony-free system) that, rather than receiving control signals and starting operation synchronously with the start of radiation image capture, detects the radiation R irradiated from the radiation generation device 12 and automatically starts operation control. The radiation R is sensed on the basis of outputs of detection sensors, with the same structure as the detection elements 100, that are embedded among the array of the detection elements 100, or outputs of detection sensors that are arrayed apart from the array of the detection elements 100. The radiation R may also be sensed on the basis of outputs of a photo sensor, using a photo sensor that detects light converted from the radiation R. Note that the present invention is not limited to the radiation image detector 14 that employs a non-synchronous system and may be applied to a radiation image detector 14 that employs a synchronous system in which the radiation image detector 14 receives control signals from the console 16 and starts operation synchronously with the start of radiation image capture.

—System Structure of the Console—

As illustrated in FIG. 3, the console 16 is constituted as a server computer, and is provided with a display 161 and a control panel 162. The display 161 is a monitor that displays control menus for the radiation image capture device 10, captured radiation images and the like. The control panel 162 is provided with a number of control buttons, switches and the like, and inputs various kinds of data, control instructions and the like. The console 16 is equipped with a CPU 163, ROM 164, RAM 165, a hard disk drive (HDD) 166, a display driver 168, a control input detection section 169 and a communication section 167.

The CPU 163 controls overall operations of the console 16. The ROM 164 stores various kinds of programs and the like, including a control program that controls operation of the console 16. The RAM 165 temporarily memorizes various kinds of data. The HDD 166 memorizes and retains various kinds of data. The display driver 168 controls displays of various kinds of data at the display 161. The control input detection section 169 detects operation states of the control panel 162. The communication section 167 exchanges various kinds of data such as exposure conditions and the like with the radiation generation device 12, and exchanges various kinds of data such as radiation image data and the like with the radiation image detector 14. The communication section 167 transmits and receives data by wireless communications, similarly to the communication section 210 of the radiation image detector 14.

At the console 16, the CPU 163, the ROM 164, the RAM 165, the HDD 166, the display driver 168, the control input detection section 169 and the communication section 167 are connected to one another via a system bus (a common bus line) 170. Accordingly, the CPU 163 accesses each of the ROM 164, the RAM 165 and the HDD 166 via the system bus 170. The CPU 163 also controls displays of various kinds of data at the display 161 via the system bus 170 and the display driver 168. The CPU 163 may acquire operation states of the control panel 162 by users, via the control input detection section 169 and the system bus 170 and, via the system bus 170 and the communication section 167, the CPU 163 controls exchanges of various kinds of data with each of the radiation generation device 12 and the radiation image detector 14.

—System Structure of the Radiation Generation Device—

As illustrated in FIG. 3, the radiation generation device 12 is provided with a radiation source 121, a radiation source control section 122 and a communication section 123. The communication section 123 exchanges various kinds of data such as exposure conditions and the like with the console 16. The radiation source control section 122 controls the radiation source 121 on the basis of exposure conditions received via the communication section 123.

The radiation source control section 122 is provided with a microcomputer similar to the detector control section 208 of the radiation image detector 14. The memory of this microcomputer stores data such as exposure conditions and the like that is received via the communication section 123. Exposure conditions include at least data such as a tube voltage, a tube current and an exposure duration. The radiation source control section 122 irradiates the radiation R from the radiation source 121 in accordance with the exposure conditions.

—Apparatus Structure of the Radiation Detection Panel—

1. Overall Structure of the Radiation Detection Panel

Figure 5:
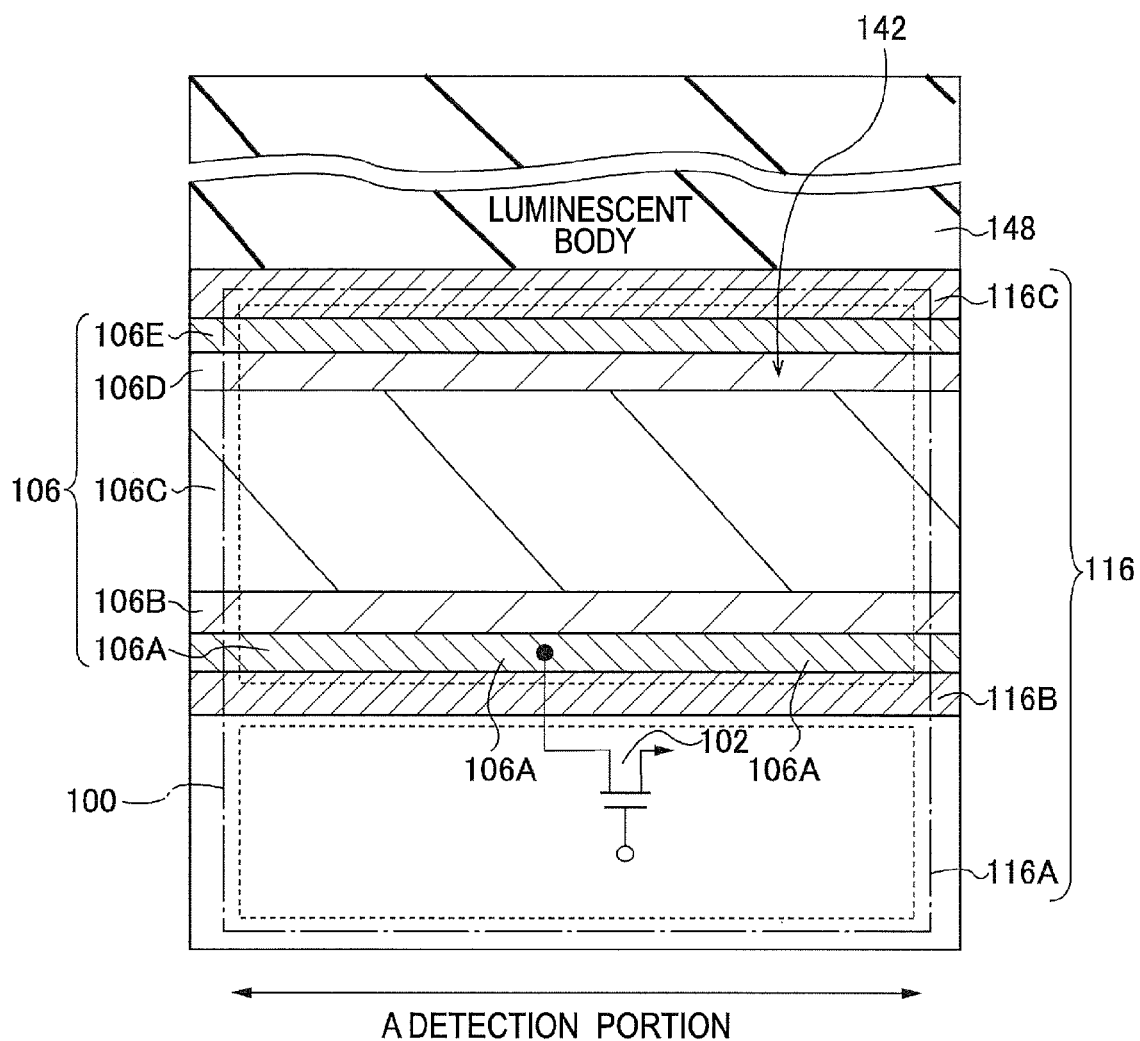
FIG. 5 is a schematic sectional diagram showing the device structure of principal portions (an optoelectronic conversion component and a luminescent body) of the radiation detection panel illustrated in FIG. 3.

As shown in FIG. 5, the radiation detection panel 142 of the radiation image detector 14 according to the first exemplary embodiment is provided with the TFT matrix board 116 and a luminescent body (scintillator) 148 that is disposed over the TFT matrix board 116 in FIG. 5. A single detection portion is appropriately illustrated in this drawing. The detection element 100 is disposed in the TFT matrix board 116. An individual detection element 100 is a single pixel, the smallest unit of resolution. The detection element 100 has a structure in which the optoelectronic conversion element 106 is provided at an insulating substrate 116A, and the optoelectronic conversion element 106 is layered on the TFT 102, which is provided on the insulating substrate 116A.

2. Structure of the Luminescent Body (Scintillator)

As shown in FIG. 5, a transparent insulating film 116C is disposed at the top layer of the TFT matrix board 116, and the luminescent body 148 is disposed over the transparent insulating film 116C. The luminescent body 148 is provided over substantially the whole area of the TFT matrix board 116.

Because the luminescent body 148 is disposed over the optoelectronic conversion element 106 with the transparent insulating film 116C therebetween, radiation R that is incident from the luminescent body 148 side (the upper side of FIG. 5) may be absorbed and converted to light, and radiation R that is incident from the insulating substrate 116A side (the lower side of FIG. 5) may also be absorbed and converted to light.

A wavelength range of light emitted by the luminescent body 148 is set in accordance with the light sensitivity of the optoelectronic conversion element 106. As an example, if a photodiode or metal-insulator-semiconductor (MIS) transistor employing the commonly used amorphous silicon (a-Si) is used for the optoelectronic conversion element 106, the wavelength range is set in the visible light range (wavelengths from 360 nm to 830 nm) in accordance with the light sensitivity characteristics of the amorphous silicon. In the radiation image detector 14, if amorphous silicon is employed at the optoelectronic conversion element 106 to enable the capture of radiation images, it is preferable if the light emitted by the luminescent body 148 includes green light, at which the light sensitivity of amorphous silicon is highest.

If X-rays are used as the radiation R and X-ray images are to be captured, it is preferable if the luminescent body 148 includes cesium iodide (CsI). It is particularly preferable if cesium iodide with thallium added thereto (CsI(Tl)), which has a light emission spectrum with a wavelength range of 400 nm to 700 nm when X-rays are irradiated at the luminescent body 148, gadolinium oxysulfide (GOS; $Gd_2O_2S$:Tb) or the like is used. CsI(Tl) has a light emission peak wavelength of 565 nm in the visible light range. The radiation R of the present invention is not limited to X-rays. Radiations that may be used include at least radiations that are used in medicine, such as gamma rays, electron beams, neutron beams, proton beams, baryon beams and the like.

In the first exemplary embodiment, the luminescent body 148 is fabricated basically as a separate member (a separate body) from the TFT matrix board 116, which is the radiation detection panel 142. The luminescent body 148 is attached to the radiation detection panel 142 in a fabrication process (assembly procedure) of the radiation image detector 14.

3. Structure of the Optoelectronic Conversion Element

Figure 6:
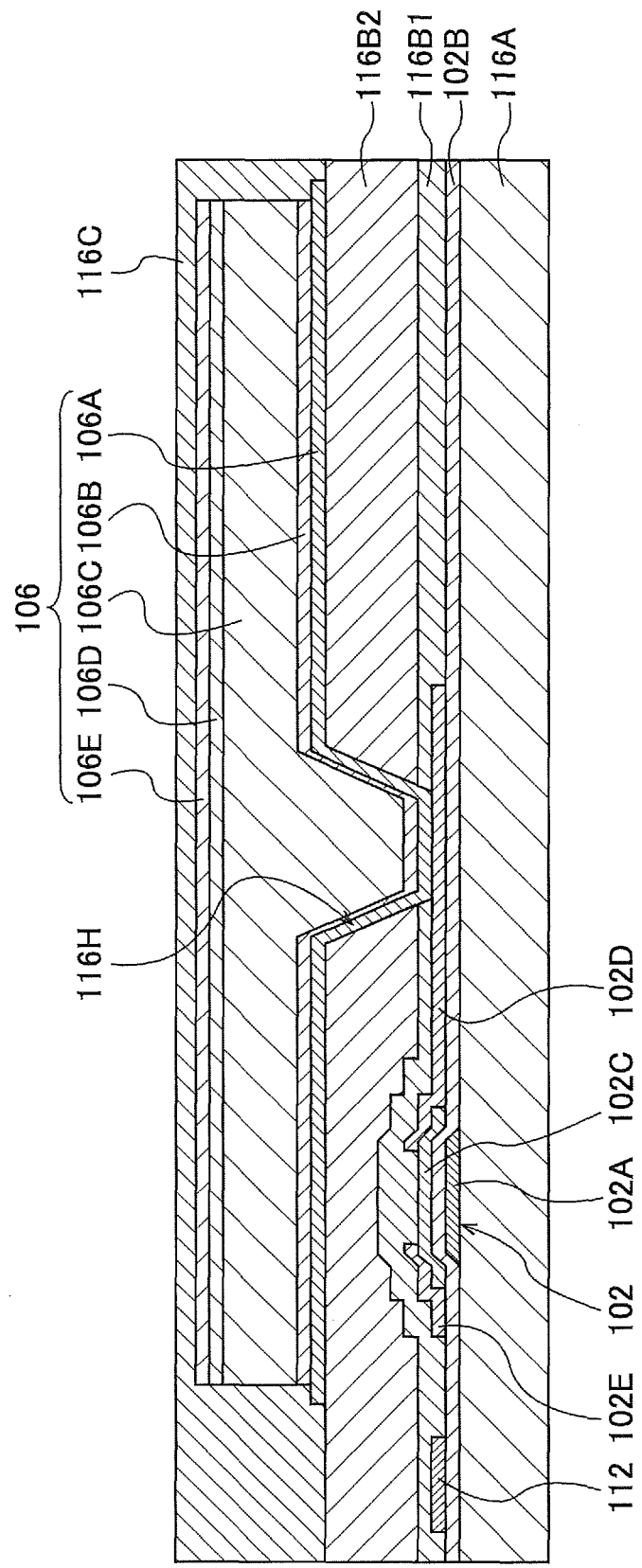
FIG. 6 is a schematic sectional diagram showing the device structure of other principal portions (a TFT and the optoelectronic conversion component) of the radiation detection panel illustrated in FIG. 3.

As shown in FIG. 5 and FIG. 6, the detection element 100 according to the present exemplary embodiment has a PIN structure, and the optoelectronic conversion element 106 that is used employs an indirect conversion system. The optoelectronic conversion element 106 is disposed on the insulating substrate 116A of the TFT matrix board 116. The optoelectronic conversion element 106 is structured by sequential layering of one electrode (a lower electrode) 106A, a first semiconductor layer 106B, a second semiconductor layer 106C, a third semiconductor layer 106D and another electrode (an upper electrode) 106E.

The electrode 106A is disposed over the insulating substrate 116A with an insulating film 116B therebetween, and is divided up between each of the detection elements 100 (each detection portion or each of pixel portions). In the first exemplary embodiment, as shown in FIG. 6, the insulating film 116B is structured by laminated films of a TFT protection film 116B1 and a flattening film 116B2 in in a layer above the TFT protection film 116B1. The TFT protection film 116B1 is, for example, a $SiN_x$ film formed by chemical vapor deposition (CVD). The flattening film 116B2 is a coated insulating film formed of a photosensitive organic material with a low conductivity.

If a film thickness of the semiconductor layers from the first semiconductor layer 106B to the third semiconductor layer 106D is thick, at around 1 μm, the material of the electrode 106A is almost unrestricted in terms of transparency or non-transparency provided the material is conductive. Thus, a transparent or non-transparent conductive material may be used for the electrode 106A. As a transparent conductive material, for example, indium tin oxide (ITO) or the like may be used. As a non-transparent conductive material, for example, an aluminium film, an aluminium alloy film, a silver film or the like may be used. However, if the film thickness of the semiconductor layers from the first semiconductor layer 106B to the third semiconductor layer 106D is thin (for example, 0.2 μm to 0.5 μm), light may not be sufficiently absorbed in the first semiconductor layer 106B to third semiconductor layer 106D. The light is illuminated onto the TFT 102, and leakage current between the main electrodes 102D and 102E of the TFT 102 increases. Accordingly, it is preferable if a conductive material or laminate thereof that is non-transparent or opaque is used for the electrode 106A.

The first semiconductor layer 106B is disposed on the electrode 106A, the second semiconductor layer 106C is disposed on the first semiconductor layer 106B, and the third semiconductor layer 106D is disposed on the second semiconductor layer 106C. The optoelectronic conversion element 106 according to the first exemplary embodiment employs a PIN structure. Thus, the first semiconductor layer 106B is formed of n+-type amorphous silicon, the second semiconductor layer 106C is formed of i-type amorphous silicon, and the third semiconductor layer 106D is formed of p+-type amorphous silicon. The second semiconductor layer 106C produces charges (pairs of free electrons and free holes) from the light converted by the luminescent body 148. The first semiconductor layer 106B is used as a contact layer and is electrically connected to the electrode 106A. The third semiconductor layer 106D is similarly used as a contact layer and is electrically connected to the electrode 106E.

The electrode 106E is separately disposed on the third semiconductor layer 106D. A conductive material with high transparency such as, for example, ITO, indium zinc oxide (IZO) or the like may be used for the electrode 106E. Although not illustrated in FIG. 5 and FIG. 6, wiring that supplies a fixed potential is connected to the electrode 106E.

In the first exemplary embodiment, the optoelectronic conversion element 106 is constituted to include the electrodes 106A and 106E in addition to the first semiconductor layer 106B, second semiconductor layer 106C and third semiconductor layer 106D. The optoelectronic conversion element 106 may also employ an MIS structure.

4. Structure of the TFT

As shown in FIG. 6, the TFT 102 of each detection element 100 is disposed on the insulating substrate 116A in a region below and corresponding with the electrode 106A of the optoelectronic conversion element 106. In a plan view seen from a direction perpendicular to the surface of the insulating substrate 116A, the TFT 102 is disposed in a region superposed with the electrode 106A of the optoelectronic conversion element 106. That is, the TFT 102 and the optoelectronic conversion element 106 are laminated three-dimensionally over the insulating substrate 116A. Thus, the area of the insulating substrate 116A of each detection element 100 and the area occupied by the detection element 100 in directions in the same plane may be minimized.

The TFT 102 is provided with the gate electrode 102A, a gate insulation film 102B, an active layer (channel layer) 102C, the one main electrode (drain electrode) 102E and the other main electrode (source electrode) 102D. The gate electrode 102A is disposed on the surface of the insulating substrate 116A. In the first exemplary embodiment, the gate electrode 102A is formed in the same conductive layer as the gate lines 110, of the same conductive material. The gate insulation film 102B is disposed on the surface of the insulating substrate 116A over substantially the whole area of the insulating substrate 116A, with the gate electrodes 102A therebetween. The active layer 102C is disposed on the surface of the gate insulation film 102B and is superposed with the gate electrode 102A. The main electrodes 102D and 102E are disposed on the active layer 102C, and are separated from one another over the gate electrode 102A. In the first exemplary embodiment, the main electrodes 102D and 102E are fainted in the same conductive layer of the same conductive material.

In the radiation image detector 14 according to the first exemplary embodiment, the active layer 102C of the TFT 102 is formed of amorphous silicon. The active layer 102C may also be formed of a non-crystalline oxide. An oxide containing at least one of gallium and zinc (for example, an In—O material) may be used as a non-crystalline oxide. It is preferable if an oxide containing at least two of indium, gallium and zinc (for example, an In—Zn—O material, an In—Ga—O material or a Ga—Zn—O material) is used as a non-crystalline oxide. Even more preferably, an oxide containing indium, gallium and zinc may be used. Specifically, an In—Ga—Zn—O non-crystalline oxide is preferably a non-crystalline oxide whose composition in a crystalline state would be represented by $InGaO_3(ZnO)_m$ (m being a natural number of less than 6), and more preferably $InGaZnO_4$. If the active layer 102C is formed of a non-crystalline oxide, the TFT 102 does not absorb radiation R such as X-rays or the like, or even if it does absorb such radiation R, the radiation is only retained in tiny amounts. Therefore, the production of noise may be effectively suppressed.

In the first exemplary embodiment, a non-alkaline glass is used for liquid crystals in the insulating substrate 116A. Now, if a non-crystalline oxide is employed for the active layer 102C of the TFT 102 and an organic optoelectronic conversion material is employed in place of the semiconductor layers from the first semiconductor layer 106B to the third semiconductor layer 106D of the optoelectronic conversion element 106, film formation with low temperature processes is possible for both the active layer 102C and the organic optoelectronic conversion material. Hence, the insulating substrate 116A is not limited to being a substrate with a high heat resistance, such as a semiconductor substrate, a quartz substrate, a glass substrate or the like. A flexible substrate of plastic or the like, or a substrate using an aramid (a fully aromatic polyamide), bionanofibers or the like may be employed. Specifically, a flexible substrate of a polyester such as polyethylene terephthalate, polybutylene phthalate, polyethylene naphthalate or the like, or a polystyrene, polycarbonate, polyether sulfone, polyarylate, polyimide, polycycloolefin, norbornene resin, poly(chlorotrifluoroethylene) or the like may be used. If a flexible substrate made of such a plastic is used, the radiation image detector 14 may be reduced in weight, which enhances portability for, for example, carrying, handling and the like.

On the insulating substrate 116A, the following layers may be provided: an insulating layer for ensuring insulation; a gas barrier layer for preventing permeation of moisture, oxygen and the like; an undercoating layer for improving flatness and contact with the electrodes and the like; and so forth.

An aramid that is used as the insulating substrate 116A may be an aramid that employs a high-temperature process with a temperature of 200° C. or above. Thus, the transparent electrode material is cured at a high temperature and the resistance of the high-temperature material is lowered. An automatic mounting process, including a solder reflow process with a high temperature of 200° C. or above is applicable to a driver chip constituting the gate line driving section 200. In regard to a thermal expansion coefficient of the ITO or glass plate or the like, because the thermal expansion coefficient of aramid is low, there is little warping of the insulating substrate 116A after the completion of fabrication processes, and cracks are unlikely to occur in the insulating substrate 116A. Aramid has a high mechanical strength relative to the mechanical strength of a glass plate or the like, so the insulating substrate 116A may be made thin. The insulating substrate 116A is not limited to a single-layer plate structure; a compound plate structure in which an aramid is layered on an ultra-thin glass plate may also be employed.

A bionanofiber that is used as the insulating substrate 116A may be a composite with a transparent resin of cellulose microfibril strands (bacterial cellulose) produced from a bacteria (an Acetobacter such as Acetobacter Xylinum). The cellulose microfibril strands have a microscopic width of, for example, 50 nm, which is about one tenth of the wavelengths of visible light, and have high strength, high resilience and low thermal expansion. The bacterial cellulose is immersed in a transparent resin such as an acrylic resin, an epoxy resin or the like, and the resin is cured. Thus, bionanofibers may be provided that contain 60-70% fibers and exhibit a transparency of about 90% for a wavelength of 500 nm The bionanofibers have a low thermal expansion coefficient (3-7 ppm) compared with silicon crystal, have a strength comparable with steel (460 MPa) and a high resilience (30 GPa), and are flexible. Therefore, the insulating substrate 116A may be made thinner than one formed from a glass plate or the like.

The interlayer insulating film 116B is provided over the whole of the insulating substrate 116A, including the main electrodes 102D and 102E of the TFTs 102. The electrode 106A of each optoelectronic conversion element 106 is electrically connected with the main electrode 102D via a connection hole 116H formed in the interlayer insulating film 116B.

Figure 7:
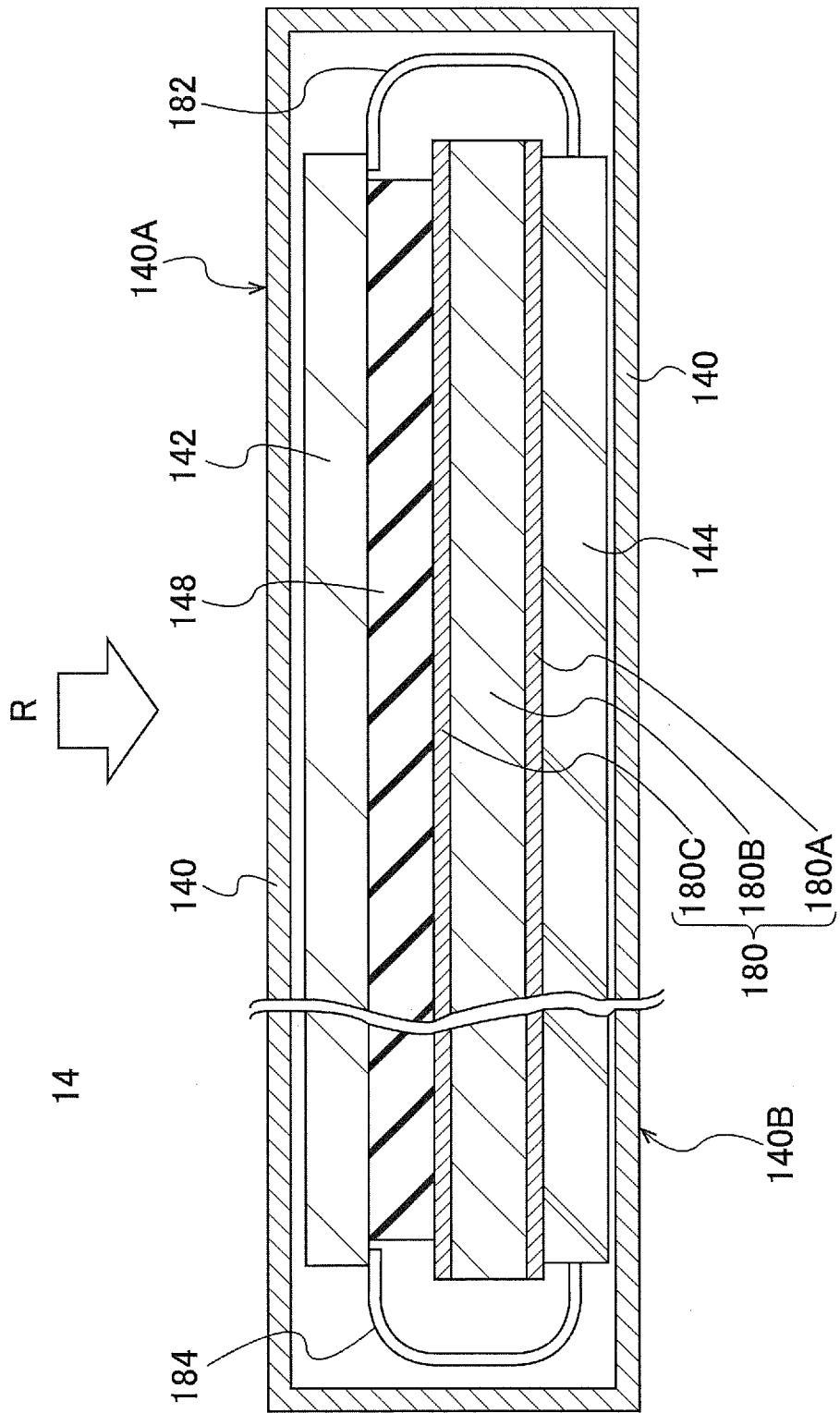
FIG. 7 is a sectional diagram showing a concrete structure of the radiation image detector shown in FIG. 2.

—Apparatus Structure of the Radiation Detector—
1. Overall Schematic Structure of the Radiation Image Detector As shown in FIG. 7, the radiation image detector 14 is provided with the radiation detection panel 142, the signal processing board 144, flexible printed circuits (FPCs) 182 and 184, and the casing 140. Respective one ends of the flexible printed circuits 182 and 184 are electrically connected to the radiation detection panel 142 and the other ends are electrically connected to the signal processing board 144. The casing 140 accommodates the radiation detection panel 142 and the signal processing board 144, and accommodates the flexible printed circuits 182 and 184 with spacing thereof from the interior walls.

The radiation image detector 14 according to the first exemplary embodiment employs an irradiation side sampling (ISS) system (incidence on the TFT board surface) in which light converted from the radiation R is read through the irradiated surface 140A side with respect to the radiation R. Thus, inside the casing 140, the radiation detection panel 142 is mounted at a top plate inner face at the rear side of the irradiated surface 140A, with the insulating substrate 116A shown in FIG. 5 and FIG. 6 opposing the irradiated surface 140A and the luminescent body 148 opposing the non-irradiated surface 140B. For the mounting, for example, double-sided adhesive tape is used. Note that the radiation image detector 14 is not limited to an ISS system; a scintillator face incidence system in which light converted from the radiation R is read through the non-irradiated surface 140B side, at the opposite side from the irradiated surface 140A with respect to the radiation R, may also be employed.

The radiation image detector 14 according to the first exemplary embodiment is provided with a reinforcement member 180 inside the casing 140. The reinforcement member 180 principally functions to enhance the mechanical strength of the casing 140. The reinforcement member 180 is disposed at a central region in the direction of thickness of the casing 140, and is arranged substantially in parallel with the irradiated surface 140A and non-irradiated surface 140B of the casing 140. The reinforcement member 180 is a plate-shaped member with an area a bit smaller than the irradiated surface 140A and non-irradiated surface 140B.

In the first exemplary embodiment, the reinforcement member 180 is provided with a chassis 180A, a reinforcement plate 180B and a deposition plate 180C. These are formed in a three-layer structure layered in this order from the non-irradiated surface 140B toward the irradiated surface 140A. The chassis 180A is a chassis of, for example, aluminium, whose thickness is set to 0.3 mm to 0.5 mm. The reinforcement plate 180B is a reinforcement plate of, for example, carbon, whose thickness is set to 1.1 mm to 1.3 mm. The deposition plate 180C is a deposition plate of, for example, aluminium, whose thickness is set to 0.2 mm to 0.4 mm.

The radiation detection panel 142 is disposed at the irradiated surface 140A side of the reinforcement member 180 with the luminescent body 148 therebetween. The thickness of the radiation detection panel 142 is not particularly limited, but is here set to, for example, 0.6 mm to 0.8 mm. The thickness of the luminescent body 148 is set to, for example, 0.5 mm to 0.7 mm.

The signal processing board 144 is disposed at the non-irradiated surface 140B side of the reinforcement member 180. In FIG. 7, the signal processing board 144 is schematically illustrated as a single structural element (component). In practice, however, the signal processing board 144 is a wiring board at which circuits are mounted to respectively constitute the gate line driving section 200, signal processing section 202, temperature sensor 204, image memory 206, detector control section 208, communication section 210 and power supply section 212 shown in the above-described FIG. 3. The circuits include integrated circuit (chips), resistance elements, capacitance elements, condensers and the like. As an example, a printed wiring board is used for the wiring board. The circuits may be separated between and mounted on a plural number of wiring boards.

2. Structure of the Casing

As shown in FIG. 7, the casing 140 is a hollow cuboid, including the irradiated surface 140A, which is a top plate, the non-irradiated surface 140B, which is a bottom plate separated from and opposing the irradiated surface 140A, and side portions (side plates) disposed along edge portions of the irradiated surface 140A and non-irradiated surface 140B. In the radiation image detector 14 according to the first exemplary embodiment, in order to keep the effects of magnetic noise from the exterior to a minimum, at least outer side surfaces and inner side surfaces of the casing 140 are insulators. The meaning of at least the surfaces being insulators includes both the whole of the casing 140 being insulative and the main body of the casing 140 being conductive with the surfaces being made insulative (an insulating treatment being applied to the surfaces). For example, the former case corresponds to the casing 140 being fabricated of an insulating resin, and the latter case corresponds to the casing 140 being fabricated by forming an oxide coat on the surfaces of a main body made of, for example, aluminium, the surfaces of the same kind of main body being coated with an insulating coating, or the like.

In the first exemplary embodiment, a material that may realize light weight and high stiffness is selected for the casing 140, in order to improve handling characteristics of the radiation image detector 14. In accordance with these requirements, a carbon fiber reinforced plastic (CFRP) in which carbon fiber is coated with an insulating resin is used for the casing 140. The insulating resin that is used is, for example, an epoxy resin.

3. Structure of the Flexible Plate

As shown at the right side of FIG. 7, the flexible printed circuit 182 is a wiring cable that electrically connects the data lines 112 of the radiation detection panel 142 with the signal processing section 202 mounted at the signal processing board 144. Describing this in more detail using FIG. 8 and FIG. 9, one end of the flexible printed circuit 182 (terminals 182C1 in FIG. 9) is electrically connected to external terminals of the data lines 112 that are protruded at a periphery edge portion of the radiation detection panel 142. For the electrical connection, for example, a heat-and-pressure connection method is used in which a connection medium, such as an anisotropic conductive connector, an anisotropic conductive sheet, an anisotropic conductive film, an anisotropic conductive rubber or the like, is interposed and both heat and pressure are applied thereto. The other end of the flexible printed circuit 182 (terminals 182C2 in FIG. 9) is electrically connected to external terminals of the signal processing section 202 that are protruded at a periphery edge portion of the signal processing board 144. A heat-and-pressure connection method similar to that described above is used for this electrical connection. Only one of the flexible printed circuit 182 is illustrated in FIG. 7. In practice, however, a plural number of the flexible printed circuit 182 are arrayed along the edge of the radiation detection panel 142.

A central portion of the flexible printed circuit 182 protrudes away from a side face of the radiation detection panel 142 and a side face of the signal processing board 144 toward the inner wall of a side portion of the casing 140. The central portion of the flexible printed circuit 182, utilizing its flexibility, turns around in a curve so as to describe an arc. When no external force acts on the radiation image detector 14 (when the radiation image detector 14 is in a stationary state), there are small gaps between the side faces of the radiation detection panel 142, the reinforcement member 180, the signal processing board 144 and the inner wall of the side portion of the casing 140, at which gaps the flexible printed circuit 182 is separated from these to some extent and does not touch them. The dimensions of the spacings are set to, for example, a few millimeters.

Figure 8:
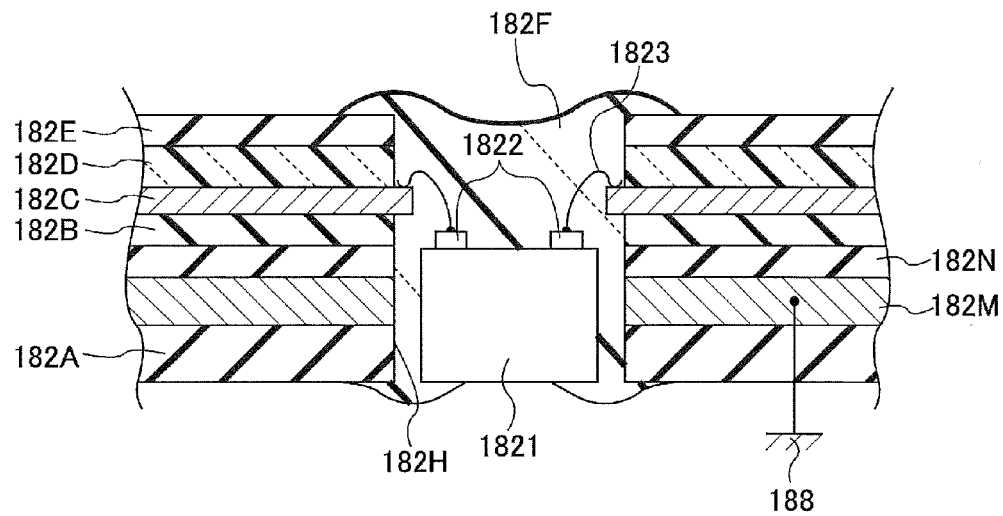
FIG. 8 is a schematic sectional diagram showing a concrete structure of a flexible printed circuit of the radiation image detector shown in FIG. 7.
Figure 9:
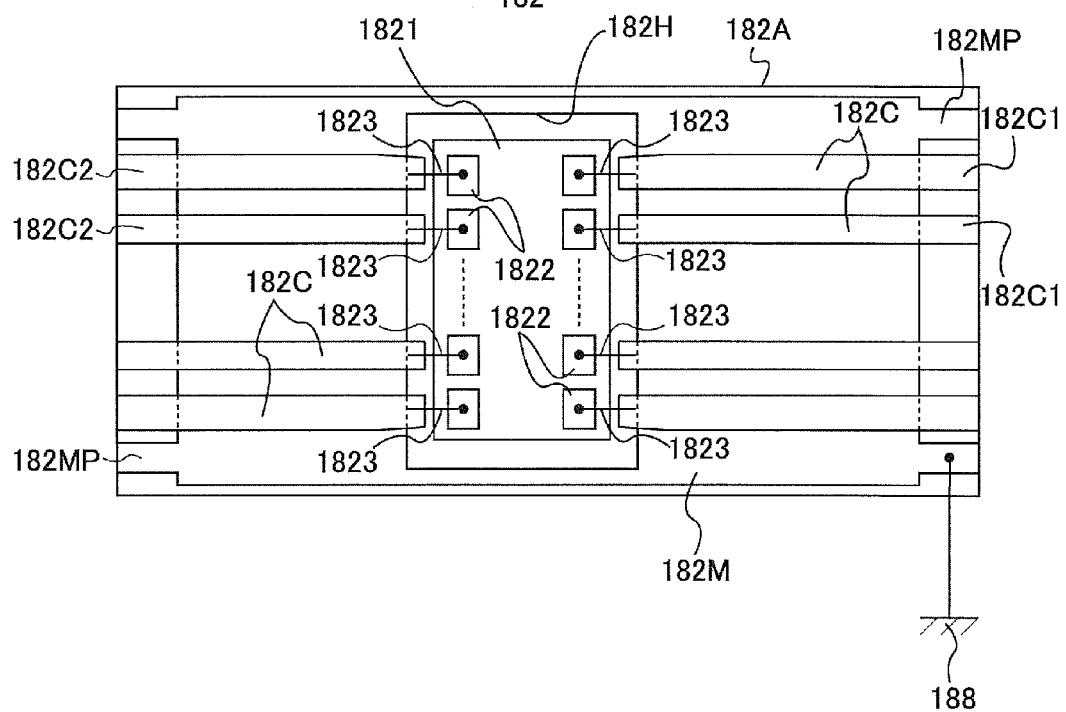
FIG. 9 is a plan diagram of the flexible printed circuit shown in FIG. 8.

The flexible printed circuit 182 according to the first exemplary embodiment is a tape carrier package (TCP) circuit board. As shown in FIG. 8 and FIG. 9, the flexible printed circuit 182 is structured by a base film 182A, an adhesive layer 182B, wiring 182C, a resist layer 182D and a coating layer 182E being sequentially layered in this order from the bottom to the top in FIG. 8. A shield layer 182M and, thereabove, an insulating layer 182N are provided between the base film 182A and the wiring 182C. A semiconductor component 182I is mounted at the flexible printed circuit 182.

The base film 182A is formed of an insulating resin film with flexibility (pliability). For example, a polyimide resin film is used for the base film 182A. The adhesive layer 182B basically adheres the base film 182A to the wiring 182C. In this case however, the adhesive layer 182B adheres the insulating layer 182N to the wiring 182C. For example, an epoxy resin adhesive layer may be used for the adhesive layer 182B. The wiring 182C electrically connects the radiation detection panel 142 with the signal processing board 144 directly or via the semiconductor component 1821.

The wiring 182C is fabricated of a metallic material with excellent electrical conductivity (low resistance values) such as, for example, copper or a copper alloy or the like, and the thickness thereof is set to, for example, 15 μm to 25 μm. FIG. 9 only shows the principal layers. The terminals 182C1 that are connected to the external terminals of the radiation detection panel 142 are provided at one side (one end) of the wiring 182C, at the right side of FIG. 9. The semiconductor component 1821 is connected to the other side of the wiring 182C. The semiconductor component 1821 functions as, for example, charge amplifiers (the sample-hold circuits 220) that amplify the radiation image data propagated through the data lines 112 of the radiation detection panel 142. The semiconductor component 1821 may also perform, for example, some of the functions of the signal processing section 202.

The semiconductor component 1821 is disposed in an opening (penetrating hole) 182H that is formed in a central portion of the flexible printed circuit 182. The other side of the wiring 182C protrudes in the form of finger leads into the opening 182H, and is electrically and mechanically connected with external terminals (bonding pads) 1822 of the semiconductor component 1821 by wires 1823 that are bonded using, for example, a wire bonding method.

The terminals 182C2 that connect to the external terminals of the signal processing board 144 are provided at one side of the wiring 182C at the left side of FIG. 9 (the other end), and the other side is connected to the semiconductor component 1821. The other side of the wiring I 82C is electrically and mechanically connected to others of the external terminals 1822 of the semiconductor component 1821 using, for example, others of the wires 1823.

The resist layer 182D is disposed on the wiring 182C and is fabricated of, for example, a urethane resin. The coating layer 182E is formed to serve as a final protection layer, and is fabricated of, for example, a polyimide-based resin layer.

The shield layer 182M is disposed to be superposed with the whole area of the wiring 182C, apart from regions of the terminals 182C1 connecting with the radiation detection panel 142 and the terminals 182C2 connecting with the signal processing board 144, and the region of the opening 182H in which the semiconductor component 1821 is disposed. Fixed potential take-out terminals 182MP are formed by portions of the shield layer 182M protruding at regions at one end and the other end of the flexible printed circuit 182, which are regions at which the terminals 182C1 and 182C2 of the flexible printed circuit 182 are arrayed. A fixed potential 188 is connected to the shield layer 182M through these fixed potential take-out terminals 182MP. If a fixed potential is supplied to any of the wiring 182C of the flexible printed circuit 182 of the first exemplary embodiment, this fixed potential is used as the fixed potential 188. If the heat-and-pressure connection method is used, then provided the fixed potential take-out terminals 182MP are electrically connected with the terminal 182C1 or terminal 182C2 of a wire of the wiring 182C that is connected to the fixed potential 188, the shield layer 182M is connected to the fixed potential 188. The fixed potential 188 is a ground for the circuits provided in the flexible printed circuit 182 (for example, a ground or 0 V power supply potential). An operating power supply potential for the circuits (a power supply potential higher than 0 V) may also be used for the fixed potential 188.

The shield layer 182M utilizes a potential that is the fixed potential 188 used at the radiation detection panel 142 or a potential that is the fixed potential 188 used at the signal processing board 144 and supplies the fixed potential 188 from either thereof. The shield layer 182M may use a ground of the casing 140 as the fixed potential 188 and be connected to this fixed potential 188. Further, provided there are no variations in the potential, a negative potential may be used for the fixed potential 188.

In the first exemplary embodiment, the shield layer 182M is fabricated of the same conductive material as the wiring 182C, in order to lower resistance and immediately eliminate static electricity (charges) caused by electrostatic charging. For similar reasons, the thickness of the shield layer 182M is set to be thicker than the thickness of the wiring 182C by, for example, around 15 μm to 25 μm.

The insulating layer 182N is disposed between the shield layer 182M and the wiring 182C, and prevents electrical short circuits between the two. For example, an epoxy-based resin layer may be used for the insulating layer 182N.

In order to protect the semiconductor component 1821 from the external environment, the opening 182H of the flexible printed circuit 182 is filled with a sealing material 182F. For example, a polyimide-based resin fabricated by a drip-application method (potting) may be used for the sealing material 182F.

The flexible printed circuit 184 is a wiring cable that electrically connects the gate lines 110 of the radiation detection panel 142 with the gate line driving section 200 mounted at the signal processing board 144, as shown at the right side of FIG. 7. In the first exemplary embodiment, at a minimum, the shield layer 182M is disposed at the flexible printed circuit 182 at which misdetections of radiation image data (analog signal charges) due to electrostatic charging have substantial effects. With a view to using common components and reducing the total number of components, the flexible printed circuit 184 is constituted with the same structure as the flexible printed circuit 182. Another semiconductor component 1821 that is mounted at the flexible printed circuit 184 is different from the semiconductor component 1821 mounted at the flexible printed circuit 182. One end of the flexible printed circuit 184 (corresponding with the terminals 182C1 in FIG. 9) is electrically connected to external terminals of the gate lines 110 that are protruded at a periphery edge portion of the radiation detection panel 142. The heat-and-pressure connection method is used for this electrical connection. The other end of the flexible printed circuit 184 (corresponding with the terminals 182C2 in FIG. 9) is electrically connected with external terminals of the gate line driving section 200 that are protruded at a periphery edge portion of the signal processing board 144. The heat-and-pressure connection method is used for this electrical connection. Although only one flexible printed circuit 184 is illustrated in FIG. 7, in practice a plural number of the flexible printed circuit 184 are arrayed along another edge of the radiation detection panel 142, adjacent to the edge along which the flexible printed circuits 182 are arrayed.

Similarly to the central portion of the flexible printed circuit 182, the central portion of the flexible printed circuit 184 is curved round, utilizing its flexibility, in the interior of the casing 140. When no external force acts on the radiation image detector 14, there are small gaps between the flexible printed circuit 184 and the radiation detection panel 142, the reinforcement member 180, a side face of the signal processing board 144 and the inner wall of a side portion of the casing 140, at which gaps the flexible printed circuit 184 is separated from these to some extent and does not touch them. The dimensions of the spacings are set to, for example, a few millimeters. The semiconductor component 1821 of the flexible printed circuit 184 performs some of the functions of the gate line driving section 200 (for example, as a driver chip).

—Operation of the Radiation Image Capture Device—

In the radiation image capture device 10 illustrated in the above-described FIG. 1, accelerations/decelerations and vibrations are applied to the radiation image detector 14 by external forces due to contacts and impacts associated with handling before imaging of a radiation image, with position adjustment and posture adjustment of the imaging subject 18 during and just before image capture, and the like. Depending on a degree of acceleration/deceleration or vibration, changes in position of the flexible printed circuit 182 in the radiation image detector 14 may be unable to follow changes in position of the rigid bodies of the radiation detection panel 142, the signal processing board 144 and the casing 140. Hence, the central portion of the flexible printed circuit 182 is subject to movements due to its flexibility. In association with such movements, the flexible printed circuit 182 touches the inner wall of the side portion of the casing 140 or is rubbed in accordance with a vibration. When semiconductor components are mounted at the flexible printed circuit 182, amounts of movement of the flexible printed circuit 182 are larger.

Counter-charging occurs at the wiring of the flexible printed circuit 182 due to this touching or rubbing. As shown in FIG. 8 and FIG. 9, the shield layer 182M is provided at the flexible printed circuit 182. Therefore, static electricity (charges) generated at the outer side of the base film 182A of the flexible printed circuit 182 is eliminated by the shield layer 182M connected to the fixed potential 188, and noise arising in the wiring 182C may be suppressed. Thus, electrostatic charging of the flexible printed circuit 182 may be prevented. In addition, because the shield layer 182M is interposed between the base film 182A and the wiring 182C, detachment due to touching or rubbing between the flexible printed circuit 182 and the casing is unlikely. The shield layer 182M has a structure that is sandwiched by the base film 182A and the adhesive layer 182B, and adhesive force with the resin materials above and below the shield layer 182M is high. Therefore, there is no need to make a layer thickness of the shield layer 182M any thicker than necessary, and flexibility of the flexible printed circuit 182 is not impaired. Furthermore, because the shield layer 182M is connected to the fixed potential 188, charges produced by electrostatic charging are immediately absorbed by the fixed potential 188 and the production of stray capacitances may be suppressed. Therefore, misdetections of captured radiation image data may be prevented, and delays in propagation of the radiation image data may be prevented.

Figure 10:
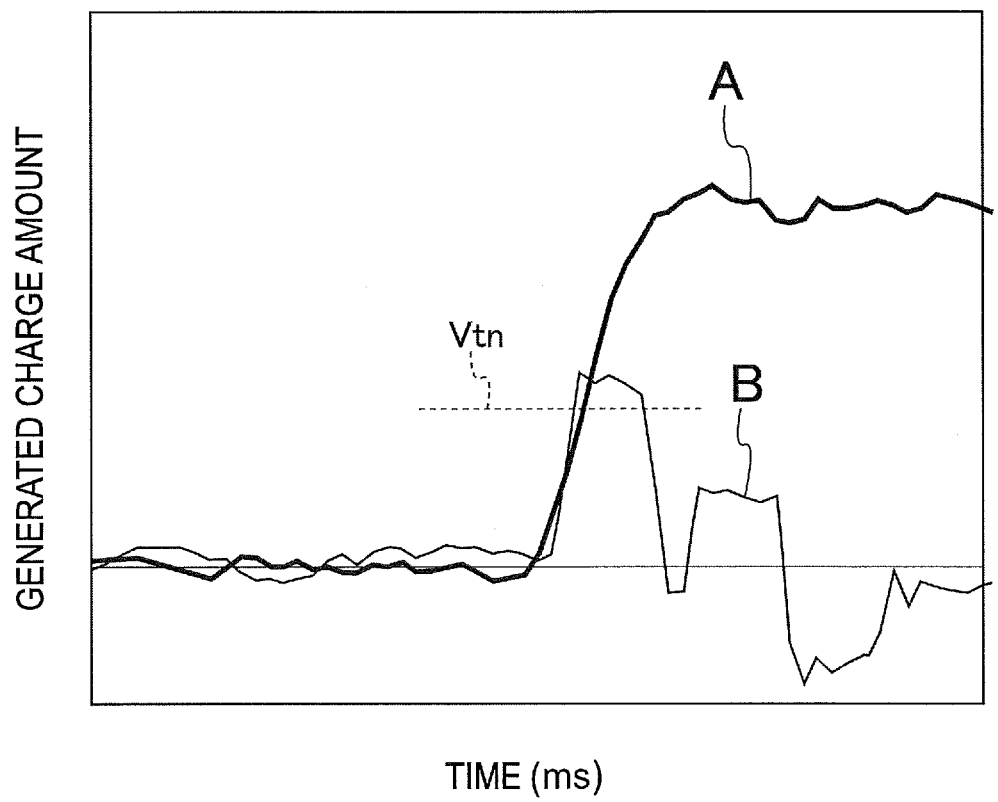
FIG. 10 is a graph showing charge amounts flowing in wiring of the flexible printed circuit before and after an irradiation of radiation in accordance with the first exemplary embodiment, and a relationship between electrostatic charging at the flexible printed circuit and the charge amounts.

FIG. 10 shows a relationship between generated charge amounts produced in the wiring of a flexible printed circuit before and after an irradiation of radiation R and generated charge amounts produced by electrostatic charging in the flexible printed circuit. In FIG. 10, the horizontal axis is time (ms) and the vertical axis is generated charge amounts. Graph A shows changes in charge amounts produced in the wiring of the flexible printed circuit 182 connected with the data lines 112 of the radiation detection panel 142 and the signal processing section 202 before and after the irradiation of radiation. Naturally, the charge amounts are greater after the radiation irradiation than before the radiation irradiation. Graph B shows changes in charge amounts of electrostatic charging in the wiring of the flexible printed circuit 182 caused by touches between the flexible printed circuit 182 and the casing 140 or vibrations associated with external forces acting during and before the radiation irradiation. If a threshold $V_{th}$ for identifying a radiation R detection signal is set to the value at which the broken line is drawn in FIG. 10, then if the wiring of the flexible printed circuit 182 is electrostatically charged and the charge amount exceeds the threshold $V_{th}$, a misdetected signal of the radiation R occurs.

—Types of Casing of the Radiation Image Detector—

Figure 11A:
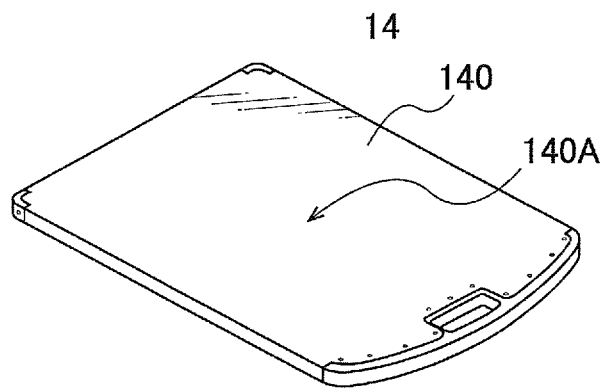
FIG. 11A is a perspective view showing a structure of the casing of the radiation image detector shown in FIG. 1.

As shown in FIG. 11A, the casing 140 of the radiation image detector 14 according to the first exemplary embodiment is formed with a frameless monocoque structure. This type of casing 140 provides the cover (front face, rear face and side faces) with the mechanical strength that a conventional frame would provide, and is suitable for reduced weight. The overall shape of this casing 140 is easily deformed by external forces, and contact with the flexible printed circuit 182 is likely to occur. Therefore, the shield layer 182M connected to the fixed potential 188 according to the first exemplary embodiment is useful in this monocoque structure.

Figure 11B:
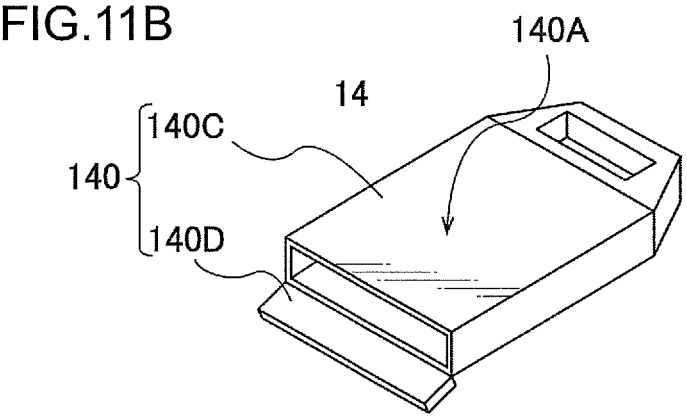
FIG. 11B is a perspective view showing another structure of the casing of the radiation image detector shown in FIG. 1.

The casing 140 shown in FIG. 11B is provided with a casing main body 140C and, at one end thereof, a lid 140D that opens and closes about a hinge. Conductive bodies 186 are provided at a position of the flexible printed circuit 182 that opposes the lid 140D and at a position of another flexible printed circuit 182 that opposes a side portion of the casing main body 140C that is at the opposite side from the lid 140D.

Figure 11C:
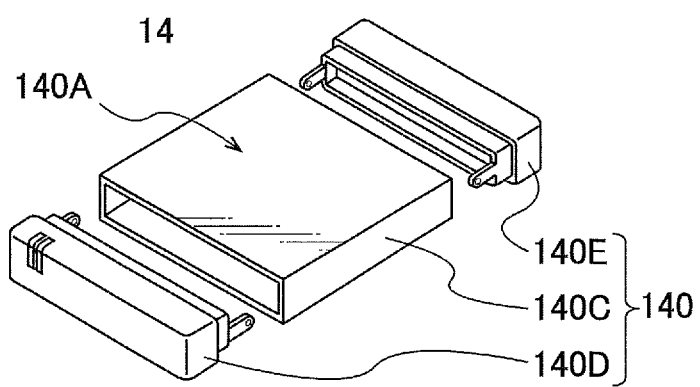
FIG. 11C is a perspective view showing another structure of the casing of the radiation image detector shown in FIG. 1.

The casing 140 shown in FIG. 11C is provided with the casing main body 140C and, at both ends thereof, lids 140D and 140E that are opened and closed by respective insertion. Arm portions protruding from each of the lids 140D and 140E engage with the inner walls of the casing main body 140C and are fixed at insertion positions. The flexible printed circuits 182 are provided at positions opposing the lids 140D and 140E.

—Operational Effects of the First Exemplary Embodiment—

As described above, in the radiation image capture device 10 according to the first exemplary embodiment, static electricity produced at the outer side of the base film 182A is eliminated by the shield layer 182M connected to the fixed potential 188, and noise arising in the wiring 182C may be suppressed. Therefore, electrostatic charging of the flexible printed circuit 182 may be prevented. In addition, because the shield layer 182M is interposed between the base film 182A and the wiring 182C, detachment of the shield layer 182M as a result of touching or rubbing between the flexible printed circuit 182 and the casing 140 is unlikely. Therefore, there is no need to make a layer thickness of the shield layer 182M any thicker than necessary, and flexibility of the flexible printed circuit 182 is not impaired. Furthermore, because the shield layer 182M is connected to the fixed potential 188, charges produced by electrostatic charging are immediately absorbed by the fixed potential 188 and the production of stray capacitances may be suppressed. Therefore, misdetections of captured radiation image data may be prevented, and delays in propagation of the radiation image data may be prevented.

In the radiation image capture device 10, the wiring 182C of the flexible printed circuit 182 may supply the fixed potential 188 to the shield layer 182M.

Further, in the radiation image capture device 10, the fixed potential 188 may be supplied to the shield layer 182M from the signal processing board 144.

Further, in the radiation image capture device 10, the fixed potential 188 may be supplied to the shield layer 182M from the radiation detection panel 142.

In the radiation image capture device 10, the shield layer 182M is provided over the whole area of the wiring 182C. Therefore, static electricity produced in most of the area of the outer side of the base film 182A is eliminated by the shield layer 182M, and noise arising in the wiring 182C may be suppressed. Thus, electrostatic charging of the flexible printed circuit 182 may be prevented.

In the radiation image capture device 10, the shield layer 182M is formed to be thicker than the wiring 182C, and electrical resistance of the shield layer 182M is set to be low. Therefore, static electricity produced at the outer side of the base film 182A is immediately eliminated and noise arising in the wiring 182C may be suppressed. Thus, electrostatic charging of the flexible printed circuit 182 may be prevented.

—First Variant Example—

The radiation image capture device 10 according to a first variant example of the first exemplary embodiment illustrates an example in which the structure of the flexible printed circuit 182 in the radiation image detector 14 of the radiation image capture device 10 according to the first exemplary embodiment described above is altered.

Figure 12:
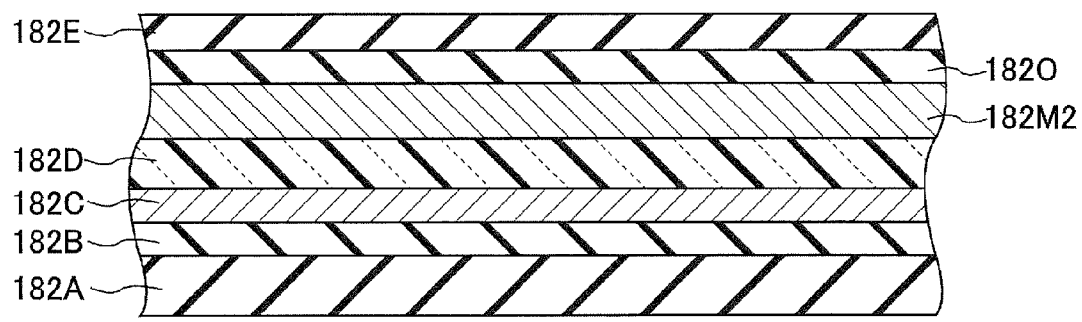
FIG. 12 is a sectional diagram of principal portions showing a concrete structure of a flexible printed circuit of a radiation image detector in accordance with a first variant example of the first exemplary embodiment.

As shown in FIG. 12, in the flexible printed circuit 182 of the radiation image detector 14 according to the first variant example, the shield layer 182M connected to the fixed potential 188 is provided between the wiring 182C and the coating layer 182E with the resist layer 182D (insulator) between the wiring 182C and the shield layer 182M. The structure, material and the like of the shield layer 182M are the same as for the shield layer 182M according to the first exemplary embodiment.

In addition, a resist layer 182O is provided between the shield layer 182M and the coating layer 182E. The resist layer 182O is fabricated of, for example, the same material as the resist layer 182D.

The radiation image capture device 10 according to the first variant example with this structure may realize the same operational effects as the operational effects provided by the radiation image capture device 10 according to the first exemplary embodiment described above. The structure of the flexible printed circuit 184 may also be altered in accordance with the alterations of the structure of the flexible printed circuit 182. The same applies to variant examples and embodiments described below.

—Second Variant Example—

The radiation image capture device 10 according to a second variant example of the first exemplary embodiment illustrates an example in which the structure of the flexible printed circuit 182 in the radiation image detector 14 of the radiation image capture device 10 according to the first exemplary embodiment described above is altered.

Figure 13:
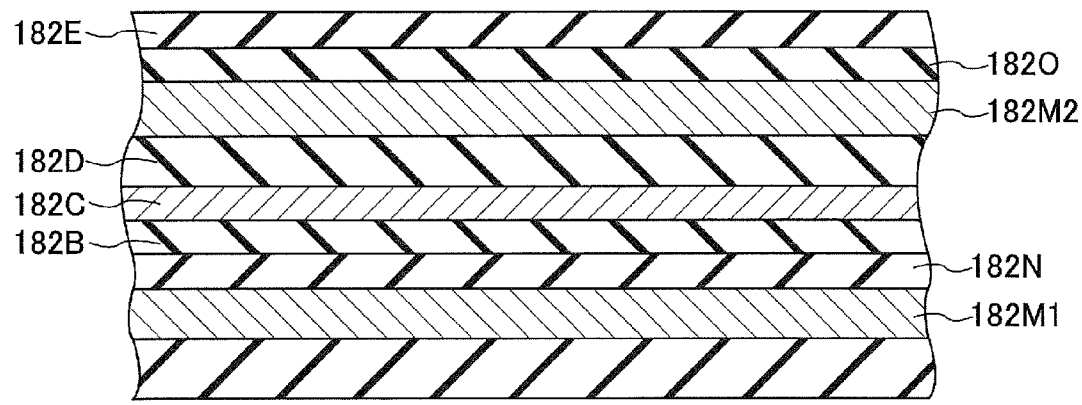
FIG. 13 is a sectional diagram of principal portions showing a concrete structure of a flexible printed circuit of a radiation image detector in accordance with a second variant example of the first exemplary embodiment.

As shown in FIG. 13, the flexible printed circuits 182 and 184 of the radiation image detector 14 according to the second variant example are provided with a shield layer 182M1 connected to the fixed potential 188 between the base film 182A and the wiring 182C, with the insulating layer 182N (insulator) between the shield layer 182M1 and the wiring 182C, and a shield layer 182M2 connected to the fixed potential 188 between the wiring 182C and the coating layer 182E, with the resist layer 182D (insulator) between the shield layer 182M2 and the wiring 182C. The structures, materials and the like of the shield layers 182M1 and 182M2 are the same as for the shield layer 182M according to the first exemplary embodiment. That is, the flexible printed circuit 182 according to the second variant example is provided with the shield layers 182M1 and 182M2 both above and below the wiring 182C.

The radiation image capture device 10 according to the second variant example with this structure may realize the same operational effects as the operational effects provided by the radiation image capture device 10 according to the first exemplary embodiment described above. In addition, because the shield layers 182M1 and 182M2 are provided at both the upper face side and the lower face side of the wiring 182C, the effect of eliminating electronic static may be improved and electrostatic charging of the flexible printed circuit 182 even more effectively prevented.

—Second Exemplary Embodiment—

A second exemplary embodiment of the present invention illustrates an example in which the structure of the flexible printed circuit 182 in the radiation image detector 14 of the radiation image capture device 10 according to the first exemplary embodiment described above is altered.

Figure 14:
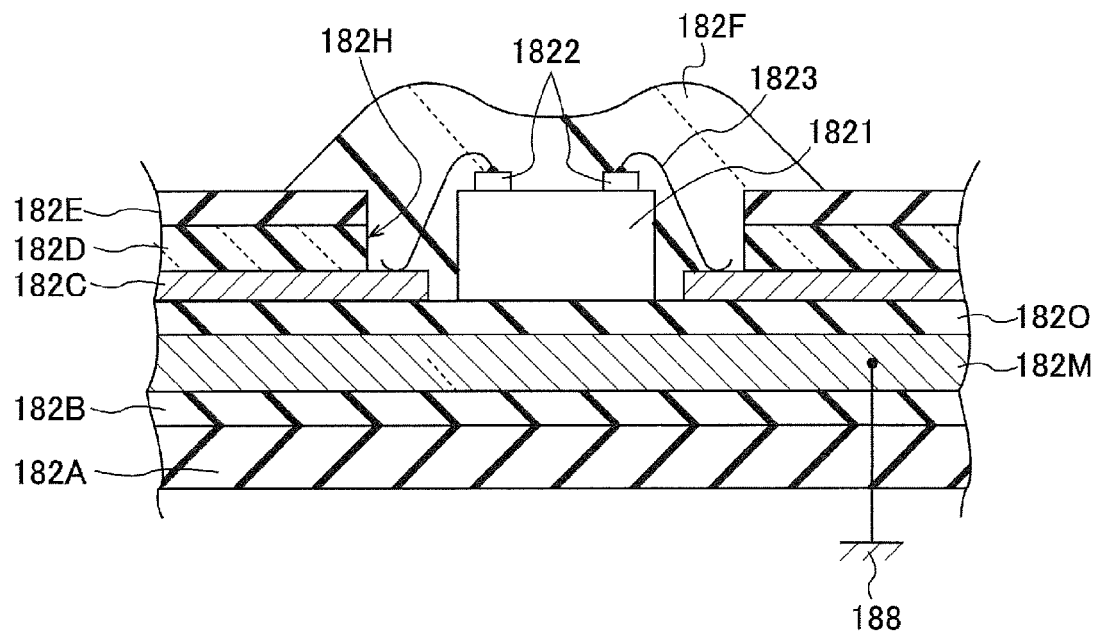
FIG. 14 is a sectional diagram of principal portions showing a concrete structure of a flexible printed circuit of a radiation image detector of a radiation image capture device in accordance with a second exemplary embodiment of the present invention.

As shown in FIG. 14, in the radiation image detector 14 of the radiation image capture device 10 according to the second exemplary embodiment, the flexible printed circuits 182 and 184 are chip on film (COF) circuit boards. The flexible printed circuit 184 is structured by the base film 182A, the adhesive layer 182B, the wiring 182C, the resist layer 182D and the coating layer 182E being respectively layered in this order from the bottom layer to the top layer in FIG. 14. The flexible printed circuit 184 is provided with the shield layer 182M between the base film 182A and the wiring 182C, and the insulating layer 182O on the shield layer 182M. Similarly to the shield layer 182M according to the above-described first exemplary embodiment, the shield layer 182M is connected to the fixed potential 188.

The semiconductor component 1821 is disposed on the resist layer 182O in the opening (a stopped hole) 182H formed in the resist layer 182D and the coating layer 182E. The wiring 182C is protruded into the opening 182H and is electrically connected to the external terminals 1822 of the semiconductor component 1821. Wires 1823 that are bonded using a wire bonding method are used for the electrical connection. The radiation image capture device 10 with this structure may realize the same operational effects as the operational effects provided by the radiation image capture device 10 according to the first exemplary embodiment described above.

—First Variant Example—

The radiation image capture device 10 according to a first variant example of the second exemplary embodiment illustrates an example in which the structure of the flexible printed circuit 182 in the radiation image detector 14 of the radiation image capture device 10 according to the second exemplary embodiment described above is altered.

Figure 15:
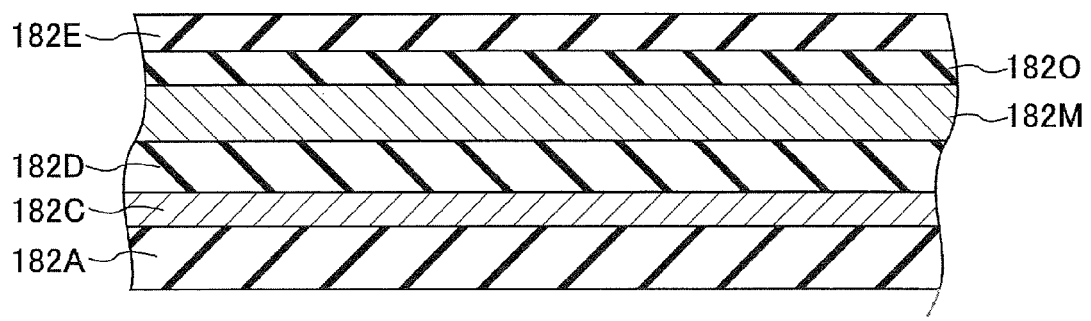
FIG. 15 is a sectional diagram of principal portions showing a concrete structure of a flexible printed circuit of a radiation image detector in accordance with a first variant example of the second exemplary embodiment.

As shown in FIG. 15, in the flexible printed circuits 182 and 184 of the radiation image detector 14 according to the first variant example, the shield layer 182M connected to the fixed potential 188 is provided between the wiring 182C and the coating layer 182E with the resist layer 182D (insulator) between the wiring 182C and the shield layer 182M. The structure, material and the like of the shield layer 182M are the same as for the shield layer 182M according to the first exemplary embodiment.

In addition, the resist layer 182O is provided between the shield layer 182M and the coating layer 182E. The resist layer 182O is fabricated of, for example, the same material as the resist layer 182D.

The radiation image capture device 10 according to the first variant example with this structure may realize the same operational effects as the operational effects provided by the radiation image capture device 10 according to the second exemplary embodiment described above.

—Second Variant Example—

The radiation image capture device 10 according to a second variant example of the second exemplary embodiment illustrates an example in which the structure of the flexible printed circuit 182 in the radiation image detector 14 of the radiation image capture device 10 according to the second exemplary embodiment described above is altered.

Figure 16:
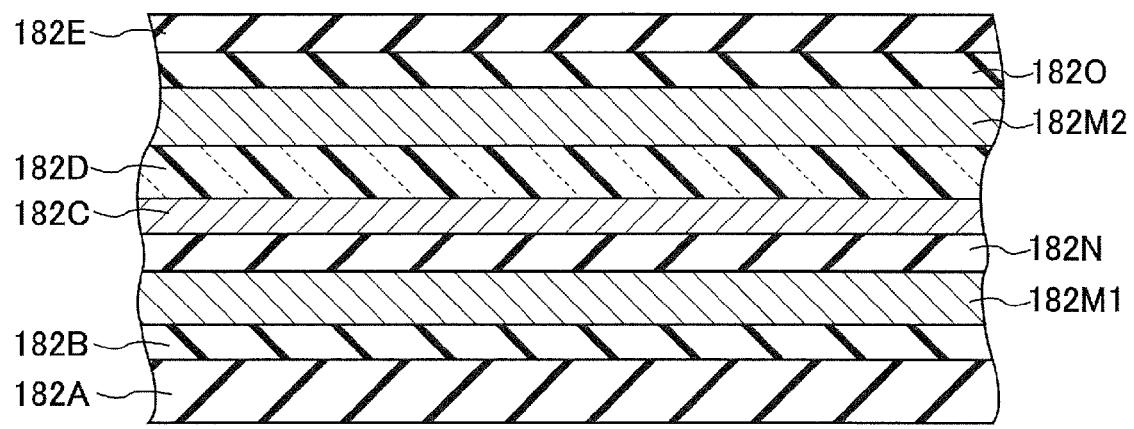
FIG. 16 is a sectional diagram of principal portions showing a concrete structure of a flexible printed circuit of a radiation image detector in accordance with a second variant example of the second exemplary embodiment.

As shown in FIG. 16, the flexible printed circuit 182 of the radiation image detector 14 according to the second variant example is provided with a shield layer 182M1 connected to the fixed potential 188 between the base film 182A and the wiring 182C, with the insulating layer 182N (insulator) between the shield layer 182M1 and the wiring 182C, and a shield layer 182M2 connected to the fixed potential 188 between the wiring 182C and the coating layer 182E, with the resist layer 182D (insulator) between the shield layer 182M2 and the wiring 182C. The structures, materials and the like of the shield layers 182M1 and 182M2 are the same as for the shield layer 182M according to the first exemplary embodiment. That is, the flexible printed circuit 182 according to the second variant example is provided with the shield layers 182M1 and 182M2 both above and below the wiring 182C.

The radiation image capture device 10 according to the second variant example with this structure may realize the same operational effects as the operational effects provided by the radiation image capture device 10 according to the second exemplary embodiment described above. In addition, because the shield layers 182M1 and 182M2 are provided at both the upper face side and the lower face side of the wiring 182C, the effect of eliminating electronic static may be improved and electrostatic charging of the flexible printed circuit 182 even more effectively prevented.

—Other Embodiments—

The present invention has been described above using the first exemplary embodiment and the second exemplary embodiments, but the present invention is not limited by these embodiments. Numerous modifications are possible within a scope not departing from the spirit of the invention. For example, the present invention may use tape automated bonding (TAB) circuit boards as the flexible printed circuits.

In a radiation image capture device according to the first aspect, static electricity generated at the outer side of the base film is eliminated by the shield layer connected to the fixed potential, and noise arising in the wiring may be suppressed. Thus, electrostatic charging of the flexible printed circuit may be prevented. In addition, because the shield layer is interposed between the base film and the wiring or between the wiring and the coating layer, detachment due to the flexible printed circuit touching, rubbing or the like against the casing is unlikely. Therefore, there is no need to make the thickness of the shield layer any thicker than necessary, and flexibility of the flexible printed circuit is not impaired. Moreover, because the shield layer is connected to the fixed potential, charges produced by electrostatic charging are immediately absorbed by the fixed potential and the generation of stray capacitances may be suppressed. Therefore, misdetections of captured radiation image data may be prevented, and delays in propagation of the radiation image data may be prevented.

In a radiation image capture device according to a second aspect, in the radiation image capture device according to the first aspect, the shield layer is disposed on the base film and is connected to the wiring, the wiring being connected to the fixed potential.

In the radiation image capture device according to the second aspect, the fixed potential may be supplied to the shield layer through the wiring of the flexible printed circuit.

In a radiation image capture device according to a third aspect, in the radiation image capture device according to the first aspect, the shield layer includes a fixed potential take-out terminal, and the fixed potential take-out terminal is connected to a fixed potential of the signal processing board.

In the radiation image capture device according to the third aspect, the fixed potential may be supplied to the shield layer from the signal processing board.

In a radiation image capture device according to a fourth aspect, in the radiation image capture device according to the first aspect, the shield layer includes a fixed potential take-out terminal, and the fixed potential take-out terminal is connected to a fixed potential of the radiation detection panel.

In the radiation image capture device according to the fourth aspect, the fixed potential may be supplied to the shield layer from the radiation detection panel.

In a radiation image capture device according to a fifth aspect, in the radiation image capture device according to any of the first to fourth aspects, the shield layer is disposed over the whole of the wiring except regions of terminals that connect to the radiation detection panel and the signal processing board.

In the radiation image capture device according to the fifth aspect, because the shield layer is provided over the whole area of the wiring, static electricity generated in a region over most of the outer side of the base film is eliminated by the shield layer, and noise arising in the wiring may be suppressed. Therefore, electrostatic charging of the flexible printed circuit may be prevented.

In a radiation image capture device according to a sixth aspect, in the radiation image capture device according to any of the first to fifth aspects, a thickness of the shield layer is thicker than a thickness of the wiring.

In the radiation image capture device according to the sixth aspect, the shield layer is formed to be thicker than the wiring. Thus, electrical resistance of the shield layer is set lower. Therefore, static electricity generated at the outer side of the base film is immediately eliminated, and noise arising in the wiring may be suppressed. Thus, electrostatic charging of the flexible printed circuit may be prevented.

In a radiation image capture device according to a seventh aspect, in the radiation image capture device according to any of the first to sixth aspects, the shield layer is provided both between the base film and the wiring and between the wiring and the coating layer.

In the radiation image capture device according to the seventh aspect, because the shield layer is provided at both an upper face side and a lower face side of the wiring, the effect of eliminating static electricity is increased, and electrostatic charging of the flexible printed circuit may be more effectively prevented.

In a radiation image capture device according to an eighth aspect, in the radiation image capture device according to any of the first to seventh aspects, the shield layer is fabricated from the same conductive material as the wiring.

In the radiation image capture device according to the eighth aspect, because the shield layer is fabricated from the same conductive material as the wiring, the shield layer may be fabricated easily.

In a radiation image capture device according to a ninth aspect, in the radiation image capture device according to any of the first to eighth aspects, the flexible printed circuit is a tape carrier package circuit board at which a semiconductor component is mounted in a component opening formed in the base film.

In the radiation image capture device according to the ninth aspect, electrostatic charging of the tape carrier package circuit board may be prevented.

In a radiation image capture device according to a tenth aspect, in the radiation image capture device according to any of the first to eighth aspects, the flexible printed circuit is a chip on film circuit board at which a semiconductor component is mounted on the base film.

In the radiation image capture device according to the tenth aspect, electrostatic charging of the chip on film circuit board may be prevented.

With the configurations described above, the present invention may provide a radiation image capture device that may suppress electrostatic charging associated with touching, rubbing and the like caused by movements of a flexible printed circuit, while avoiding detachment, not impairing flexibility, and resolving problems that lead to stray capacitances.

What is claimed is:

1. A radiation image capture device comprising:
a radiation detection panel including optoelectronic conversion elements that convert radiation to electronic signals;
a signal processing board disposed to oppose the radiation detection panel, the signal processing board performing signal processing of the electronic signals provided by the radiation detection panel;
a flexible printed circuit of which one end is electrically connected to the radiation detection panel and another end is electrically connected to the signal processing board, the flexible printed circuit including
a base film formed of an insulating resin film,
wiring disposed over the base film,
a coating layer formed of an insulating resin disposed over the wiring, and
a shield layer provided at least one of between the base film and the wiring or between the wiring and the coating layer, an insulator being interposed between the shield layer and the wiring, and the shield layer being connected to a fixed potential; and
a casing that accommodates the radiation detection panel, the signal processing board and the flexible printed circuit, wherein
the flexible printed circuit comprises a tape carrier package circuit board at which a semiconductor component is placed inside a through-hole that is formed to pass through the coating layer, the shield layer, and the base film.

2. The radiation image capture device according to claim 1, wherein the shield layer is disposed on the base film and is connected to the wiring, the wiring being connected to the fixed potential.

3. The radiation image capture device according to claim 2, wherein the shield layer is disposed over the whole of the wiring except regions of terminals that connect to the radiation detection panel and the signal processing board.

4. The radiation image capture device according to claim 2, wherein a thickness of the shield layer is thicker than a thickness of the wiring.

5. The radiation image capture device according to claim 2, wherein the shield layer is provided both between the base film and the wiring and between the wiring and the coating layer.

6. The radiation image capture device according to claim 2, wherein the shield layer is fabricated from the same conductive material as the wiring.

7. The radiation image capture device according to claim 1, wherein the shield layer includes a fixed potential take-out terminal, and the fixed potential take-out terminal is connected to a fixed potential of the signal processing board.

8. The radiation image capture device according to claim 1, wherein the shield layer includes a fixed potential take-out terminal, and the fixed potential take-out terminal is connected to a fixed potential of the radiation detection panel.

9. The radiation image capture device according to claim 1, wherein the shield layer is disposed over the whole of the wiring except regions of terminals that connect to the radiation detection panel and the signal processing board.

10. The radiation image capture device according to claim 9, wherein the shield layer is provided both between the base film and the wiring and between the wiring and the coating layer.

11. The radiation image capture device according to claim 1, wherein a thickness of the shield layer is thicker than a thickness of the wiring.

12. The radiation image capture device according to claim 1, wherein the shield layer is provided both between the base film and the wiring and between the wiring and the coating layer.

13. The radiation image capture device according to claim 12, wherein the shield layer is fabricated from the same conductive material as the wiring.

14. The radiation image capture device according to claim 1, wherein the shield layer is fabricated from the same conductive material as the wiring.

15. A radiation image capture device comprising:
a radiation detection panel including optoelectronic conversion elements that convert radiation to electronic signals;
a signal processing board disposed to oppose the radiation detection panel, the signal processing board performing signal of the electronic signals provided by the radiation detection panel;
a flexible printed circuit of which one end is electrically connected to the radiation detection panel and another end is electrically connected to the signal processing board, the flexible printed circuit including
a base film formed of an insulating resin film,
wiring disposed over the base film,
a coating layer formed of an insulating resin disposed over the wiring, and
a shield layer provided at least one of between the base film and the wiring or between the wiring and the coating layer, an insulator being interposed between the shield layer and the wiring, and the shield layer being connected to a fixed potential; and
a casing that accommodates the radiation detection panel, the signal processing board and the flexible printed circuit,
wherein the flexible printed circuit comprises a chip on film circuit board at which a semiconductor component is placed inside a through-hole that is formed on the coating layer and mounted above the shield layer.

16. The radiation image capture device according to claim 15, wherein the shield layer is disposed on the base film and is connected to the wiring, the wiring being connected to the fixed potential.

17. The radiation image capture device according to claim 15, wherein the shield layer is disposed over the whole of the wiring except regions of terminals that connect to the radiation detection panel and the signal processing board.

18. The radiation image capture device according to claim 15, wherein a thickness of the shield layer is thicker than a thickness of the wiring.

19. The radiation image capture device according to claim 15, wherein the shield layer is provided both between the base film and the wiring and between the wiring and the coating layer.

20. The radiation image capture device according to claim 15, wherein the shield layer is fabricated from the same conductive material as the wiring.

* * * * *